(12) United States Patent
Farr

(10) Patent No.: US 8,602,971 B2
(45) Date of Patent: Dec. 10, 2013

(54) OPTO-ELECTRONIC ILLUMINATION AND VISION MODULE FOR ENDOSCOPY

(75) Inventor: Mina Farr, Palo Alto, CA (US)

(73) Assignee: Vivid Medical. Inc., Pallo Alto, CA (US)

( * ) Notice: Subject to any disclaimer, the term of this patent is extended or adjusted under 35 U.S.C. 154(b) by 1331 days.

(21) Appl. No.: 12/111,107

(22) Filed: Apr. 28, 2008

(65) Prior Publication Data

US 2008/0208006 A1    Aug. 28, 2008

Related U.S. Application Data

(63) Continuation-in-part of application No. 11/233,684, filed on Sep. 23, 2005, now Pat. No. 8,480,566.

(60) Provisional application No. 60/612,889, filed on Sep. 24, 2004.

(51) Int. Cl.
*A61B 1/04* (2006.01)
*A61B 1/06* (2006.01)
*A61B 1/00* (2006.01)

(52) U.S. Cl.
USPC .......................... 600/109; 600/173; 600/129

(58) Field of Classification Search
USPC .......... 600/133, 166, 172, 175–177, 109, 174
See application file for complete search history.

(56) References Cited

U.S. PATENT DOCUMENTS

| | | | |
|---|---|---|---|
| 4,473,841 A * | 9/1984 | Murakoshi et al. ............. 348/65 |
| 5,025,778 A * | 6/1991 | Silverstein et al. ........... 600/104 |
| 5,305,121 A | 4/1994 | Moll | |
| 5,381,784 A * | 1/1995 | Adair ........................... 600/166 |
| 5,494,483 A | 2/1996 | Adair | |
| 5,538,497 A | 7/1996 | Hori | |
| 5,647,840 A | 7/1997 | D'Amelio et al. | |
| 5,836,867 A * | 11/1998 | Speier et al. .................. 600/112 |
| 5,895,350 A * | 4/1999 | Hori ............................. 600/167 |
| 6,066,090 A | 5/2000 | Yoon | |
| 6,277,064 B1 | 8/2001 | Yoon | |
| 6,648,816 B2 | 11/2003 | Irion et al. | |

(Continued)

FOREIGN PATENT DOCUMENTS

WO  PCT/US2009/041118    4/2009

OTHER PUBLICATIONS

U.S. Appl. No. 12/413,457, filed Mar. 27, 2009, Farr et al.
U.S. Appl. No. 12/759,169, filed Apr. 13, 2010, Farr et al.

(Continued)

*Primary Examiner* — Philip R Smith
*Assistant Examiner* — William Chou
(74) *Attorney, Agent, or Firm* — Maschoff Brennan

(57) ABSTRACT

Various embodiments for providing removable and pluggable opto-electronic modules for illumination and imaging for endoscopy or borescopy are provided. Generally, various medical or industrial devices can include one or more solid state or other compact electro-optic illuminating elements located thereon. Additionally, such opto-electronic modules may include illuminating optics, imaging optics, image capture devices, and heat dissipation mechanisms. The illumination elements may have different wavelengths and can be time synchronized with an image sensor to illuminate an object for imaging or detecting purpose or otherwise conditioning purpose. The optoelectronic modules may include means for optical and/or wireless communication. The removable opto-electronic modules may be plugged in on the exterior surface of a device, inside the device, deployably coupled to the distal end of the device, or otherwise disposed on the device.

32 Claims, 31 Drawing Sheets

(56) References Cited

U.S. PATENT DOCUMENTS

| | | | |
|---|---|---|---|
| 6,736,773 B2* | 5/2004 | Wendlandt et al. | 600/173 |
| 6,916,286 B2* | 7/2005 | Kazakevich | 600/173 |
| 7,029,435 B2* | 4/2006 | Nakao | 600/153 |
| 7,413,543 B2* | 8/2008 | Banik et al. | 600/129 |
| 7,591,783 B2* | 9/2009 | Boulais et al. | 600/142 |
| 2002/0143239 A1 | 10/2002 | Henzler | |
| 2002/0161283 A1 | 10/2002 | Sendai | |
| 2003/0120130 A1* | 6/2003 | Glukhovsky et al. | 600/109 |
| 2004/0039242 A1* | 2/2004 | Tolkoff et al. | 600/9 |
| 2004/0196364 A1* | 10/2004 | Takahashi | 348/65 |
| 2004/0204628 A1 | 10/2004 | Rovegno | |
| 2005/0038321 A1 | 2/2005 | Fujita et al. | |
| 2005/0096502 A1 | 5/2005 | Khalili | |
| 2005/0154262 A1 | 7/2005 | Banik et al. | |
| 2005/0182297 A1 | 8/2005 | Gravenstein | |
| 2005/0234296 A1 | 10/2005 | Saadat et al. | |
| 2005/0240077 A1 | 10/2005 | Rovegno | |
| 2005/0272975 A1* | 12/2005 | McWeeney et al. | 600/113 |
| 2006/0069314 A1 | 3/2006 | Farr | |
| 2007/0015964 A1 | 1/2007 | Eversull et al. | |
| 2007/0225561 A1 | 9/2007 | Watanabe et al. | |
| 2008/0045800 A2 | 2/2008 | Farr | |
| 2008/0051632 A1 | 2/2008 | Ito et al. | |
| 2008/0207996 A1 | 8/2008 | Tsai | |
| 2010/0198009 A1 | 8/2010 | Farr et al. | |

OTHER PUBLICATIONS

U.S. Appl. No. 12/771,087, filed Apr. 30, 2010, Farr et al.
International Search Report and Written Opinion dated Oct. 30, 2009 as issued in International Application No. PCT/US2009/041118 filed Apr. 20, 2009.
U.S. Appl. No. 11/233,684, Jul. 13, 2009, Restriction Requirement.
U.S. Appl. No. 11/233,684, Nov. 12, 2009, Office Action.
U.S. Appl. No. 11/233,684, May 14, 2010, Office Action.
International Search Report dated Apr. 23, 2012 as received in application No. PCT/US2011/052039.
Written Opinion of the International Searching Authority dated Apr. 23, 2012 as received in application No. PCT/US2011/052039.

\* cited by examiner

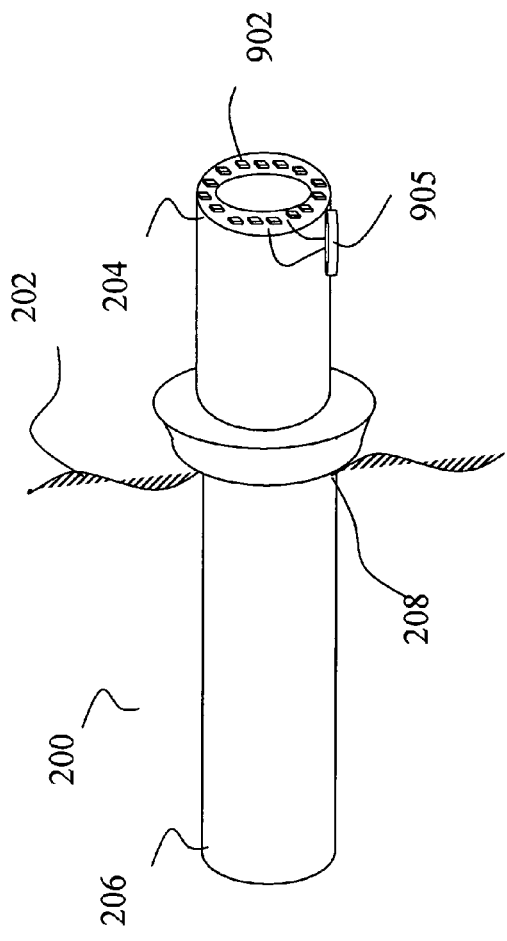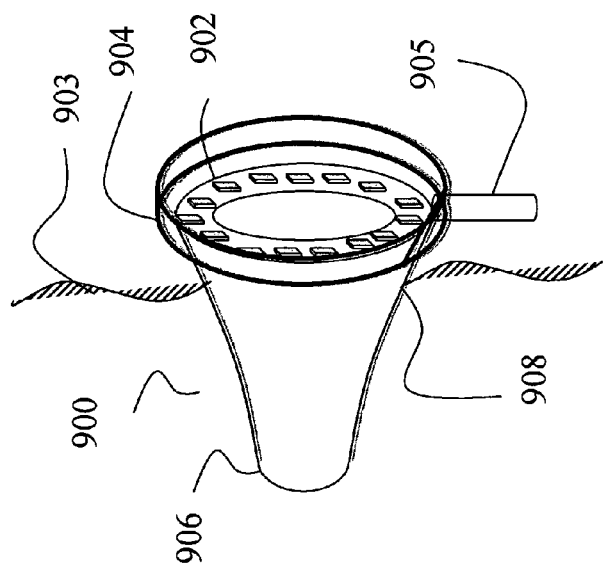
Figure 9a
Figure 9b

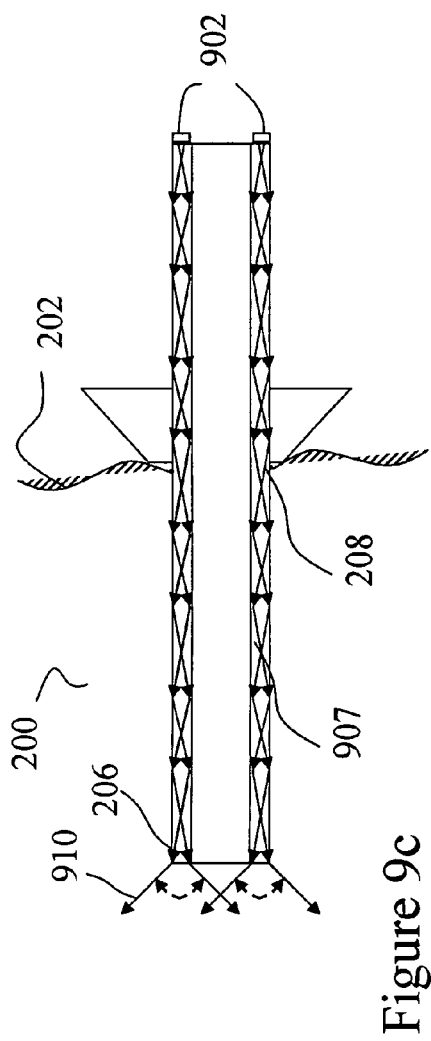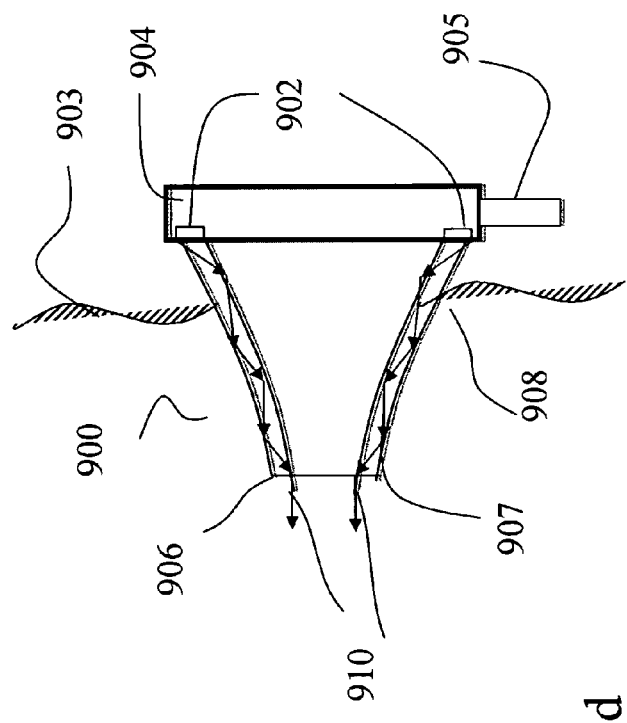
Figure 9c
Figure 9d

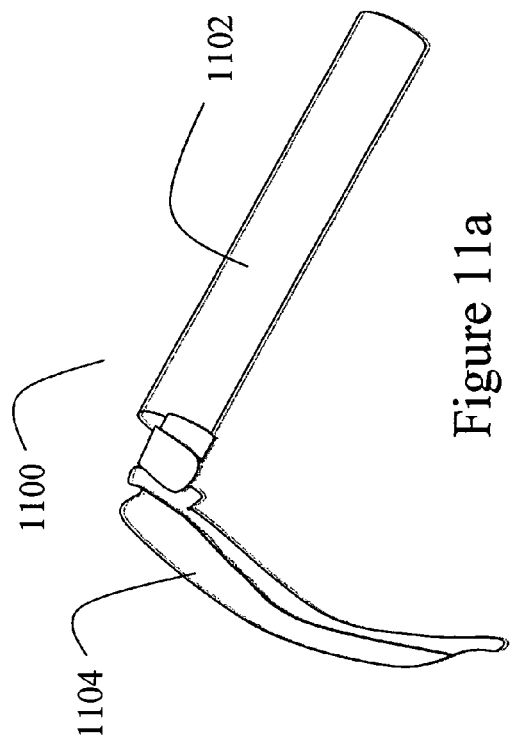
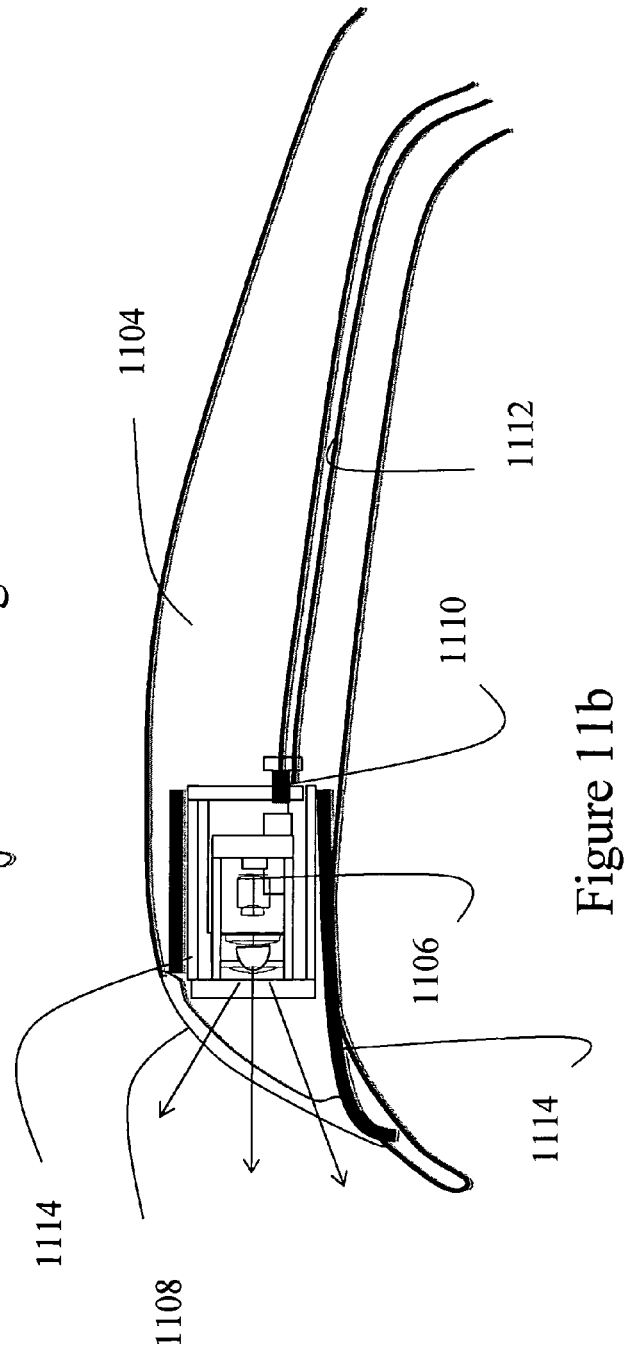
Figure 11a
Figure 11b

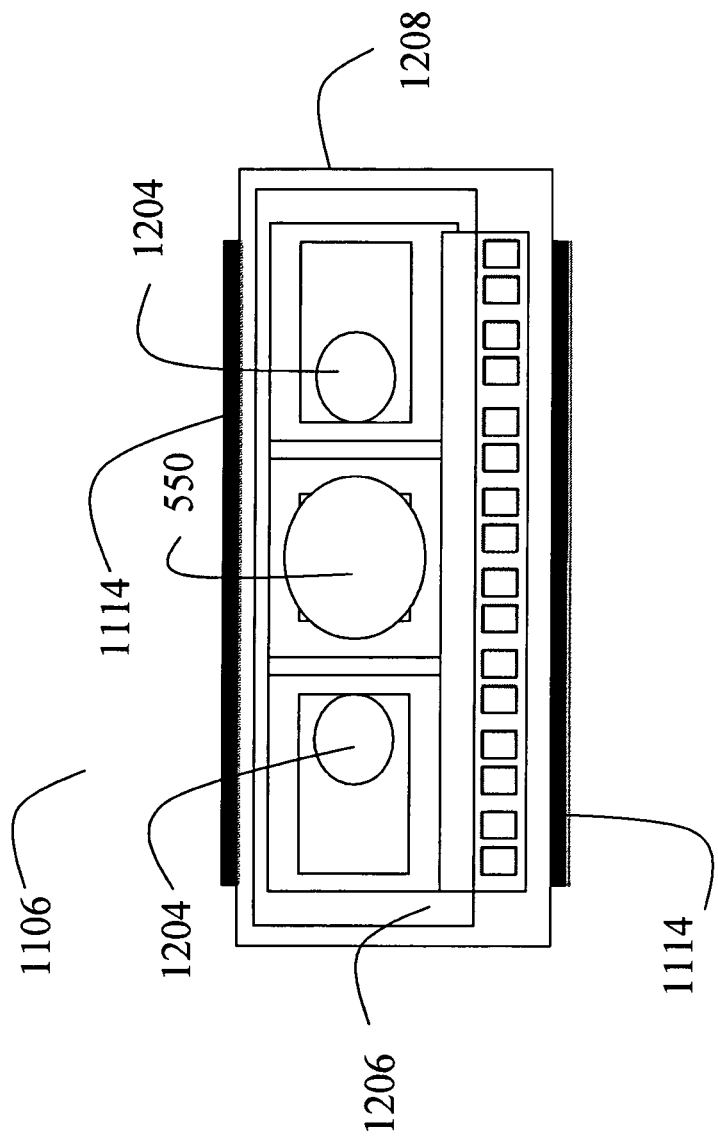

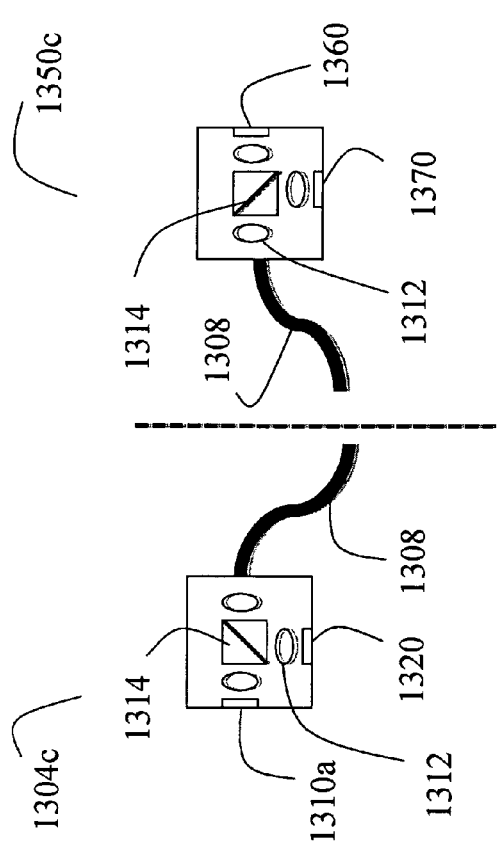
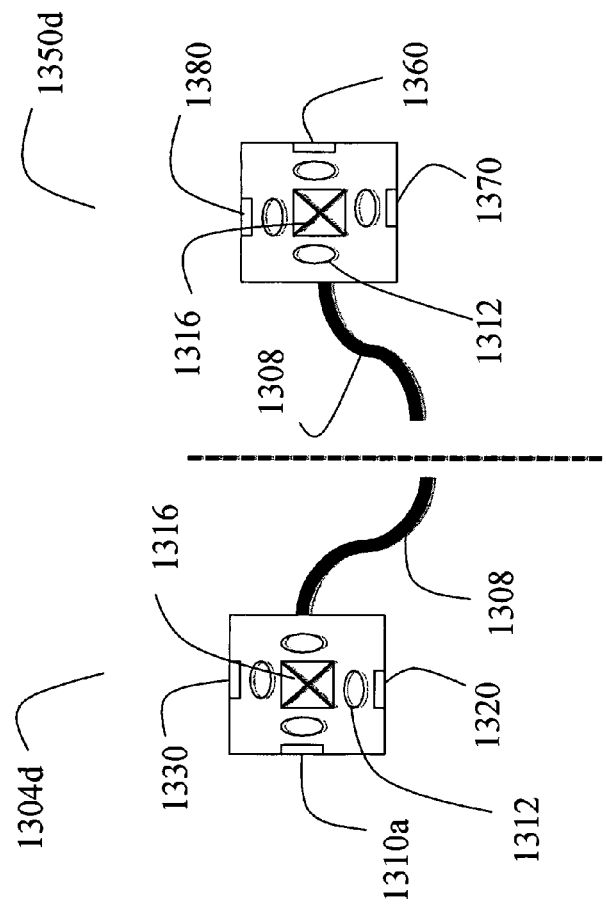
Figure 13c
Figure 13d

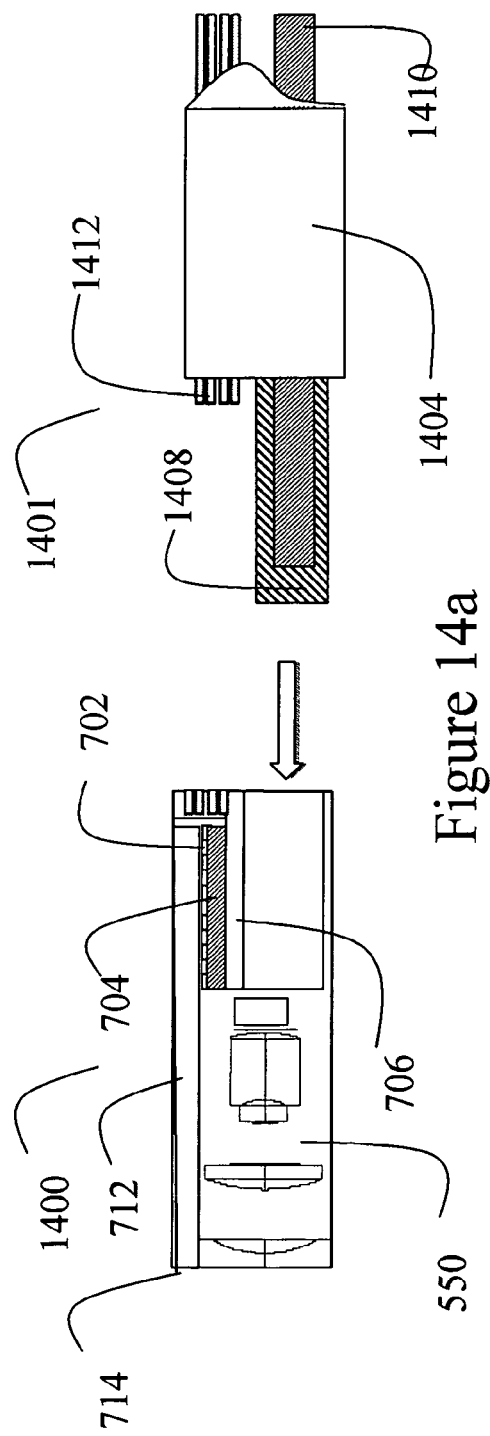
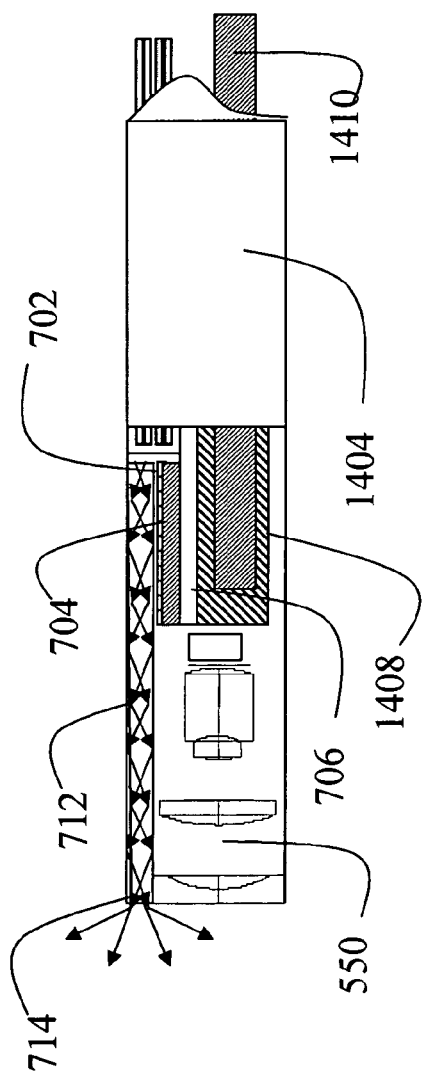
Figure 14a
Figure 14b

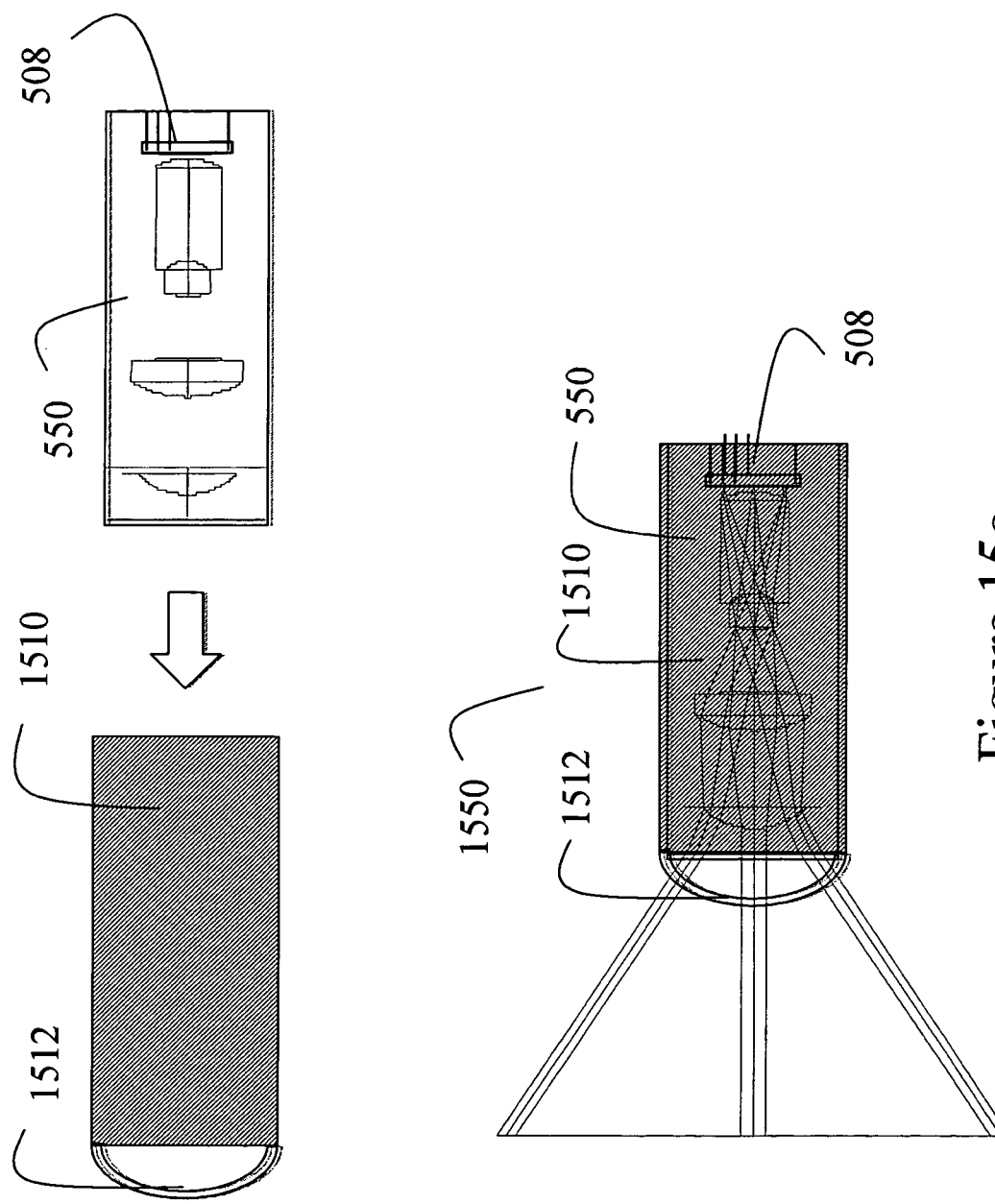

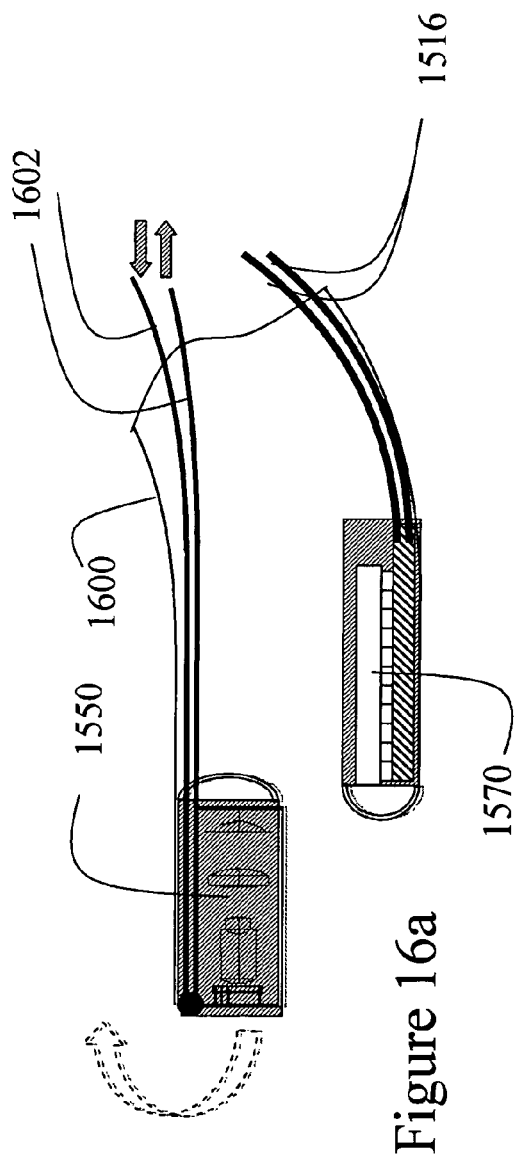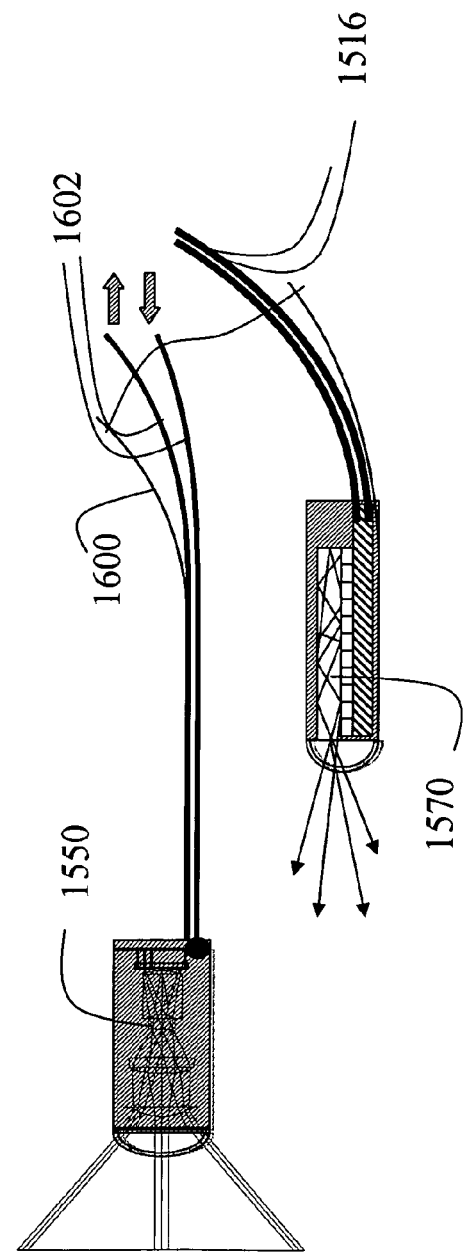
Figure 16a
Figure 16b

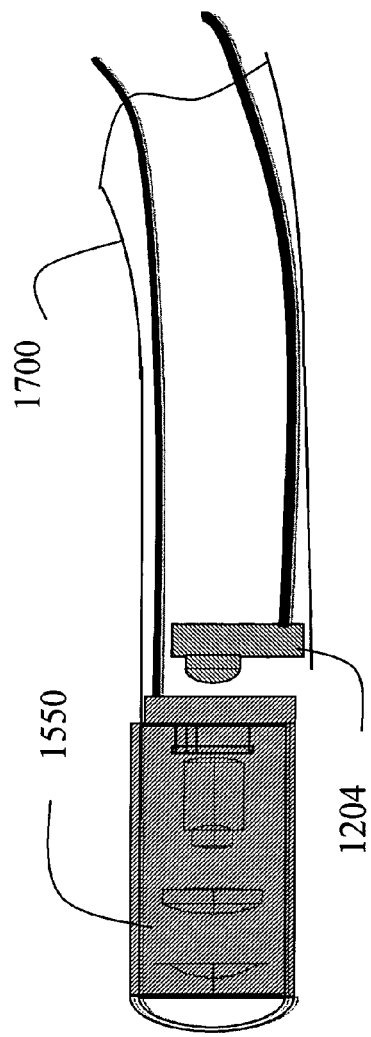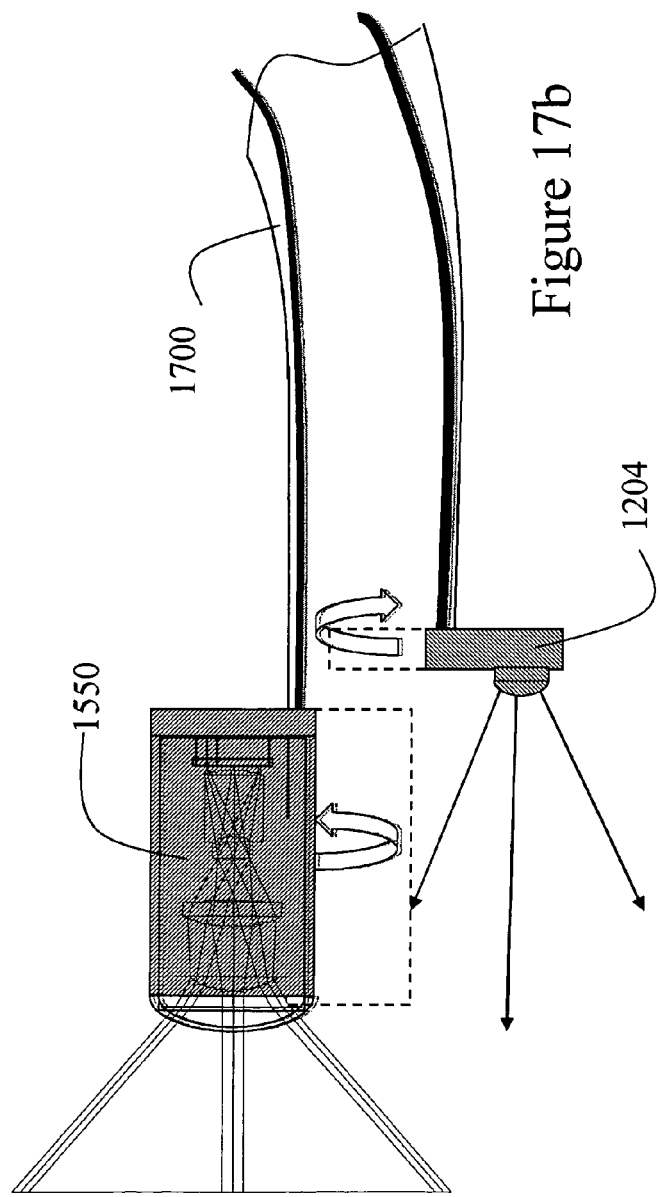

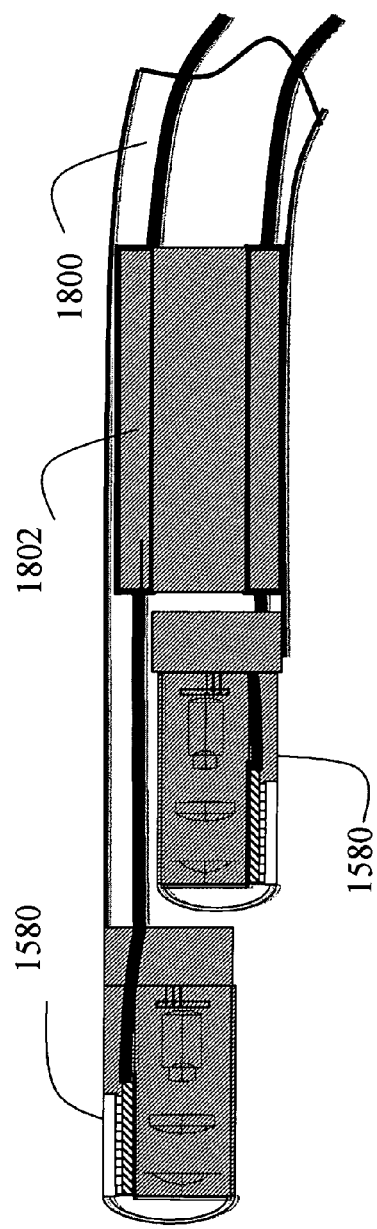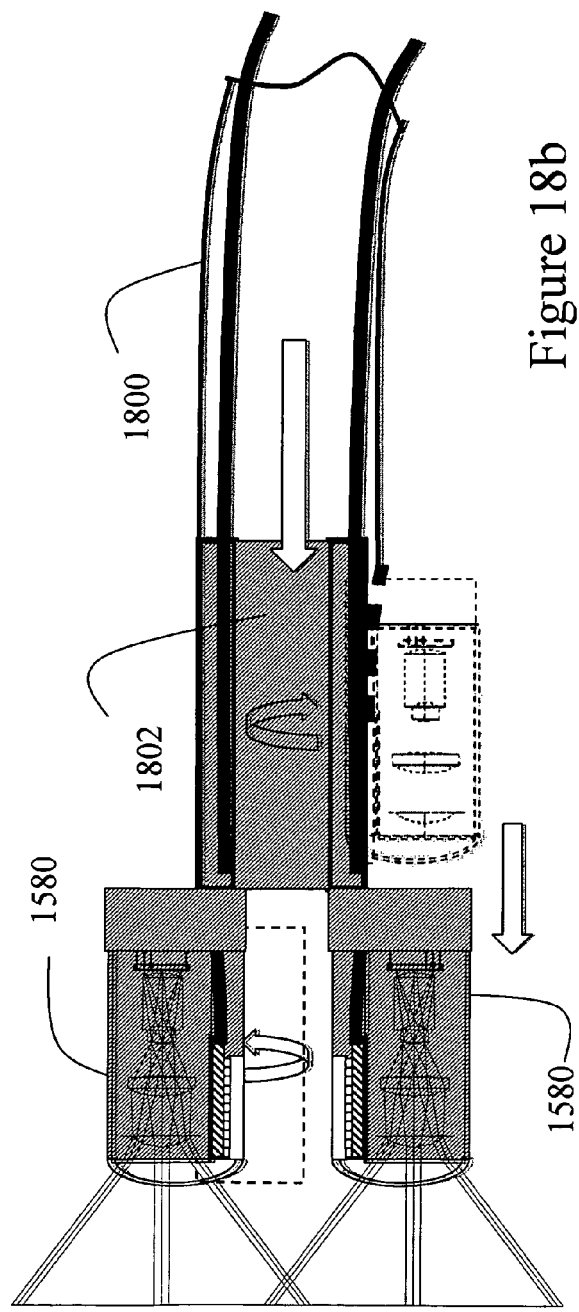

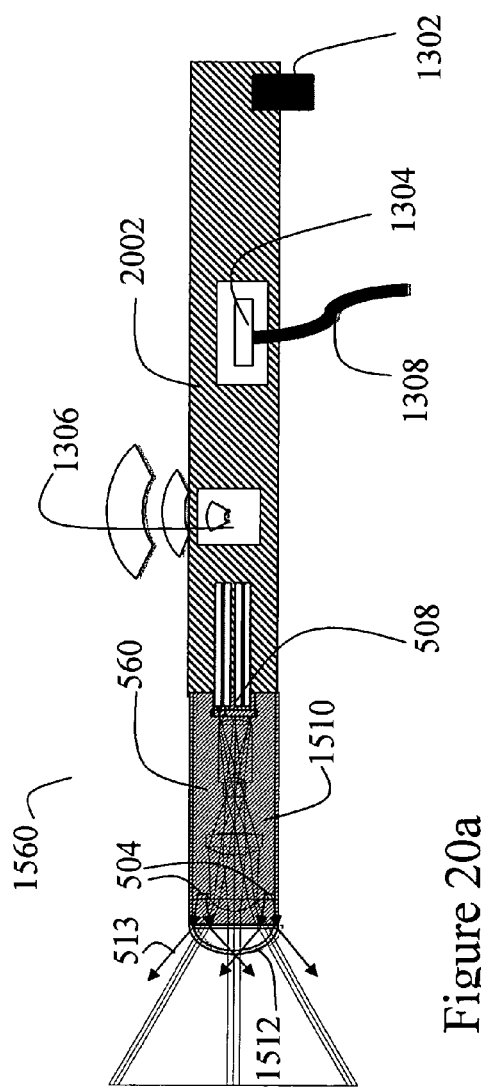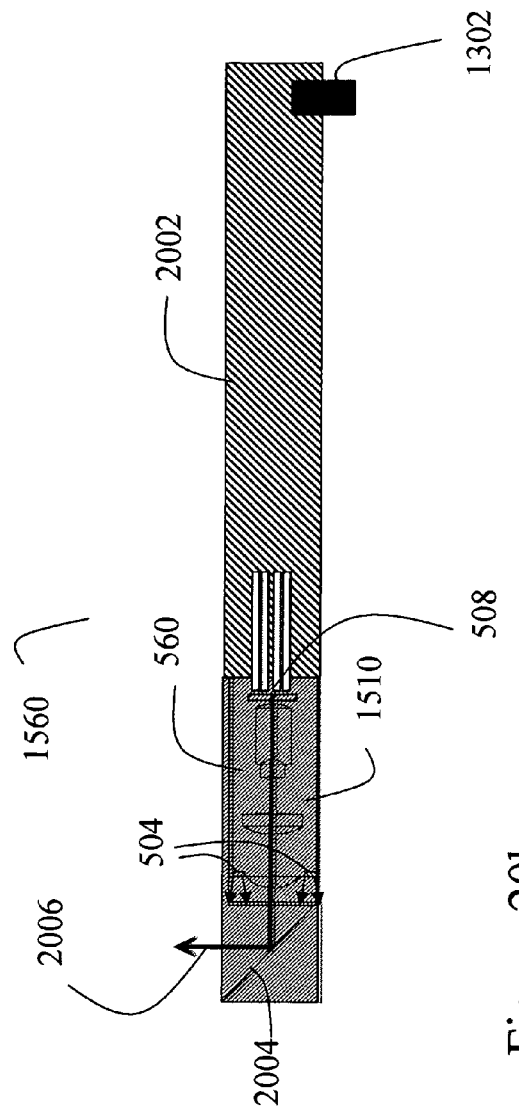
Figure 20a
Figure 20b

OPTO-ELECTRONIC ILLUMINATION AND VISION MODULE FOR ENDOSCOPY

CROSS-REFERENCE TO RELATED APPLICATIONS

This application is a continuation-in-part of U.S. patent application Ser. No. 11/233,684, filed Sep. 23, 2005 and entitled SOLID STATE ILLUMINATION FOR ENDOSCOPY, which claims the benefit of U.S. Provisional Patent Application Ser. No. 60/612,889 filed Sep. 24, 2004 and entitled "SOLID STATE ILLUMINATION FOR ENDOSCOPY," the contents of both patent applications are incorporated by reference herein in their entirety.

BACKGROUND OF THE INVENTION

1. The Field of the Invention

The present invention relates generally to apparatus for the illumination of endoscopic and borescopic fields, in minimally invasive surgical (MIS) procedures, general or diagnostic medical or industrial procedures using endoscopes or borescopes, respectively. More particularly, embodiments of the invention relate to use of removable illumination and imaging systems in endoscopic and borescopic procedures, as a means of illumination and image capture.

2. The Relevant Technology

Laparoscopy is used in both diagnostic and surgical procedures. Currently, MIS procedures, as opposed to open surgical procedures, are routinely done in almost all hospitals. Minimally invasive techniques minimize trauma to the patient by eliminating the need to make large incisions. This both reduces the risk of infection and reduces the patient's hospital stay. Laparoscopic and endoscopic procedures in MIS use different types of endoscopes as imaging means, giving the surgeon an inside-the-body view of the surgical site. Specialized endoscopes are named depending on where they are intended to look. Examples include: cystoscope (bladder), nephroscope (kidney), bronchoscope (bronchi), laryngoscope (larynx+ the voice box), otoscope (ear), arthroscope (oint), laparoscope (abdomen), gastrointestinal endoscopes, and specialized stereo endoscopes used as laparoscopes or for endoscopic cardiac surgery.

The endoscope may be inserted through a tiny surgical incision to view joints or organs in the chest or abdominal cavity. More often, the endoscope is inserted into a natural body orifice such as the nose, mouth, anus, bladder or vagina. There are three basic types of endoscopes: rigid, semi-rigid, and flexible. The rigid endoscope comes in a variety of diameters and lengths depending on the requirements of the procedure. Typical endoscopic procedures require a large amount of equipment. The main equipment used in conjunction to the visual part of the endoscopic surgery are the endoscope body, fiber optics illumination bundles, illumination light source, light source controller, imaging camera, camera control module, and video display unit.

The laparoscope is a rigid endoscope as illustrated in FIG. 1. It allows for visualization of the abdominopelvic cavities for diagnostic or surgical techniques. The laparoscope is inserted into the peritoneal cavity via a cannula that runs through the abdominal wall. There are many different features of laparoscopes, such as the size and field of vision, which determine the effectiveness of the instrument.

As illustrated in FIG. 1, the basic laparoscope is made up of a long thin tube 101 with an eyepiece 103 at one end for viewing into the patient. Fiber optic light introduced to the endoscope at fiber port 102, and launched into fiber optics 302 (FIG. 3), passes through the endoscope body 101, illuminating the area 304 that is being observed, as illustrated by radiation pattern 306 in FIG. 3. Laparoscopes are characterized by diameter and the direction of view. The direction of view is the angle 107 between the axis 105 of the laparoscope and the center field of view 106, as illustrated in FIG. 1. Typical endoscopes have lengths of approximately 30 cm and diameters in the range of 4 to 10 mm. Laparoscopes consist of two important lenses, the ocular lens at the eyepiece and the objective lens 308 at the distal end of the endoscope 300 in FIG. 3. Other lens sets acting as relay lenses 310 in FIG. 3, are used in-between the objective lens and the eye piece or the CCD camera or image position 312. Imaging rays 314 traverse the length of the scope through all the imaging optics.

The rigid endoscope also comes in different viewing angles: 120 degree or retrograde, for viewing backward; 90 degree and 70 degree for lateral viewing; 30 degree (104 as illustrated in FIG. 1) and 45 degree for forward oblique views; and 0 degree for forward viewing. The angle of the objective lens 308 used is determined by the position of the structure to be viewed.

Other surgical instruments and tools are also inserted into the body, for the operation and specific surgical manipulation by the surgeon. The insertion is done through open tubes provided inside the endoscope body for instrument insertion, such as in gastrointestinal endoscopes, or through separate incisions in the abdominal or chest wall 202, as illustrated in FIG. 2, using cannula 200 (straight or curved stainless steel or plastic tubes which are inserted into a small opening or incision in the skin). The cannula opening at the proximal end 204 outside the body is used to guide different instruments inside the body, where they are exposed to the inside of body at the distal end 206 of the cannula. Cannulas can make a seal at the incision site 208.

In a typical gastrointestinal endoscope, a tool opening is provided at the distal end of the scope, where inserted medical instruments gain access to the body following the scope body.

Endoscopes can be diagnostic, for observation only, or operative, having channels or ports for irrigation, suction, and the insertion of accessory instruments when a surgical procedure is planned. Thus, endoscope bodies also could provide mechanical or electrical control sections, buttons for valves such as a suction valve, a CO2 valve, a water bottle connector, a water feed, a suction port, etc. The common component that all endoscopes must be equipped with is a light guide section for illumination.

An illustration showing typical endoscope optics is shown in FIG. 3. Common imaging sections of the endoscope are an ocular or eyepiece, relay lenses 310 (in the case of rigid scopes), a flexible imaging fiber-optic bundle (in the case of flexible scopes), and an objective lens system 308. Endoscopes are either used as stand alone units, with the surgeon looking into the scope from the ocular or eye piece of the endoscope, or in conjunction with digital cameras, where an image of the surgical site is incident on the image capture device (charge coupled device or CCD) of the camera. Using a display device, the surgeon performs the operation looking at the image on the video monitor.

With recent technology improvements in the field of electronic imaging reducing the size of the image capture device (e.g., CCD), some endoscopes used in MIS and diagnostic procedures are equipped with a high resolution distal end camera system, commonly referred to as Chip on a Stick, one example of which is illustrated in FIG. 4 as camera system 400. These flexible endoscopes use a CCD chip 402 at the distal end of the endoscope directly capturing the image through the objective lens 404, in which case the flexible part 406 of the endoscope body contains only power and communication wires for the CCD camera at the distal tip, rather than imaging optics 408 located in a rigid portion 404 of the endoscope. Light guides 410 running the length of the endoscope are still necessary for this type of electronic scope to provide adequate lighting 412 of the surgical site 414 for imaging purposes.

Other, more complicated MIS systems make use of robotic surgical tools and instruments, and/or provide stereoscopic images of the surgical site for the surgeon, improving the surgeon's dexterity, precision and speed of operation. In these more sophisticated MIS imaging applications more specific types of illumination systems or multiple illuminators are used.

Color CCD cameras use alternate color dies on the individual CCD pixels, to capture color images. Green and red, and green and blue pixels are alternated in rows. This spatial color sampling limits the color resolution of the color CCD cameras, since each pixel is dedicated to capturing a single color in the color image.

3 chip CCD cameras (red CCD chip, blue CCD chip, and green CCD chip) are also used in high resolution applications, where all the pixels in each CCD are dedicated to detecting the single color content of the image. The individual color captured images from the 3 CCDs are then put together electronically, as the multi-color image is reproduced on the viewing display. Three chip CCD cameras are expensive and bulky.

Recent advances in illumination and image capture technology demonstrate the rapid changes that can occur in the capabilities of emerging illumination and imaging systems. For instance, very compact high mega pixel cameras are currently being incorporated widely in cellular phone cameras, whereas just a few years ago this was not possible. It is quite likely that other technological advances in imaging and illumination will occur that can be used in endoscopic medical devices. And, although it may be desirable to incorporate the latest technological advances in illumination and imaging into an endoscopic medical device, this is often impossible without designing and purchasing a brand new replacement device having the improved technology. This complete new solution, however, can be prohibitively expensive especially in the circumstances that the medical providers are under high pressure to reduce cost. Incorporation of the advanced high quality opto-electronics in current and future low cost medical procedures can also be nearly impossible.

Due to delicate and complicated nature of current endoscope illumination and vision technology, current high performance endoscopes are often limited in sterilization capability, and for the major part not autoclavable. This shortcoming not only limits the life time of these endoscopes to limited number of procedures, but also creates possibility of infection with multiple sterilization and disinfection procedures performed on the current scopes.

BRIEF SUMMARY OF THE INVENTION

These and other limitations are overcome by embodiments of the invention which relate to removable and pluggable illumination and vision systems that can be coupled to the distal end or housed within the body of various medical devices, including various endoscopic devices used as single use disposable unit, or autoclavable medical devices used in minimally invasive surgical and other diagnostic procedures. Removable and pluggable illumination and vision systems according to some embodiments of the invention include one or more solid state light sources, illumination optics (such as wave guides) and optionally include imaging optics and image capture devices, collectively referred to as Opto-Electronic (OE) illumination and vision modules. Removable and pluggable OE illumination and vision modules may additionally include accompanying electronics for process and transfer of the image. Embodiments of the invention also relate to the layouts and functionality of such removable and pluggable vision systems within the body of a disposable endoscope or other disposable medical devices, or with a disposable container housing the removable and pluggable OE illumination and vision modules. Embodiments of the invention additionally relate to general layouts of such removable and pluggable vision systems incorporating mechanisms enabling hyper Field of View (FOV) visual systems.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

To further clarify the above and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIGS. 9a, 9b, 9c, and 9d illustrate various embodiments of a self-lighted cannula or speculum using multiple LED sources installed at the proximal end of the cannula or speculum;

FIG. 11a illustrates a laryngoscope with attached laryngoscope blade for manual visualization of the larynx;

FIG. 11b illustrates a curved disposable laryngoscope blade equipped with pluggable rectangular box shaped OE illumination and vision module;

FIG. 12a illustrates a front view of the OE illumination and vision module incorporated inside the visual laryngoscope blade depicted in FIG. 11b, through the laryngoscope blade visual window with heat conduction mechanism;

FIGS. 13b, 13c and 13d represent details and possible variations to the optical link depicted in FIG. 13a;

FIGS. 14a and 14b illustrate a cylindrical shape pluggable OE illumination and vision module, with electrical and thermal connective attachment to a cylindrical shape medical device body;

FIG. 15c illustrates the pluggable cylindrical shape OE vision module from FIG. 5b, being inserted into a cylindrical protective cover with a hemispherical optically transparent window;

FIGS. 17a and 17b illustrate possible side rotational deployment of OE lensed LED illuminator, and the pluggable OE vision module with protective cover depicted in FIG. 15c, that is stored within the body of a flexible endoscope or flexible medical device body;

FIGS. 18a and 18b illustrate possible side rotational outward deployment of a pair of pluggable OE illumination and vision modules with protective cover depicted in FIG. 15f, that are stored within the body of an endoscope, and their subsequent lengthwise alignment of the deployed OE vision modules to capture stereo images of a scene;

FIG. 20a illustrates the pluggable OE illumination and vision module of FIG. 5c, plugged on a portable handle with possible wireless, optical and electrical connections;

FIG. 20b illustrates the portable device of FIG. 18a, plugged with a side viewing OE illumination and vision module;

DETAILED DESCRIPTION OF THE EXEMPLARY EMBODIMENTS

Example embodiments of the invention are directed to removable solid state opto-electronic illumination modules, that can include monochromatic, polychromatic visible, Ultra Violet (UV), and/or Infra Red (IR) solid state light sources such as high power Light Emitting Devices (LEDs) and Laser Diodes as a means of illumination in diagnostic or surgical endoscopic procedures, or functional borescopic systems.

In various endoscope geometries, it is also possible to install and remove the opto-electronic imaging system along with the removable LED illuminator systems, allowing implementation of a removable and pluggable opto-electronic or electro-optic (OE or EO) illumination and vision module, as described more fully below. The removability and pluggability of such OE vision modules described herein provide instantly upgradeable illumination and image capture systems without any necessity to replace an entire medical or other functional device still having a remaining useful life.

Advantageously, with the OE vision module removed from the medical device that houses the pluggable OE vision module, the medical device can be made autoclavable, which is a highly desirable safety feature not currently available to many endoscopes.

In particular, these removable and pluggable OE illumination and vision modules can be incorporated with a protective disposable cover, at the distal end of single use disposable endoscope, borescope, surgical or industrial tools, the tip end of single use cannulas, or the body of other disposable medical procedure functional devices. They can also be incorporated in an illumination body that is inserted separately, or in conjunction with a lighted or dark scope, into the body. The illumination of an object inside a body, a body herein being defined as at least a portion of a human, animal or physical object not easily accessible, is performed to detect the modified light, image the object, or manipulate a change in the object. The OE illumination and vision module schemes of the present invention can replace, or can be used in addition to, the conventional fiber optic illumination system and other diagnostic devices such as ultrasound imaging used in endoscopy and borescopy.

Figure 1:
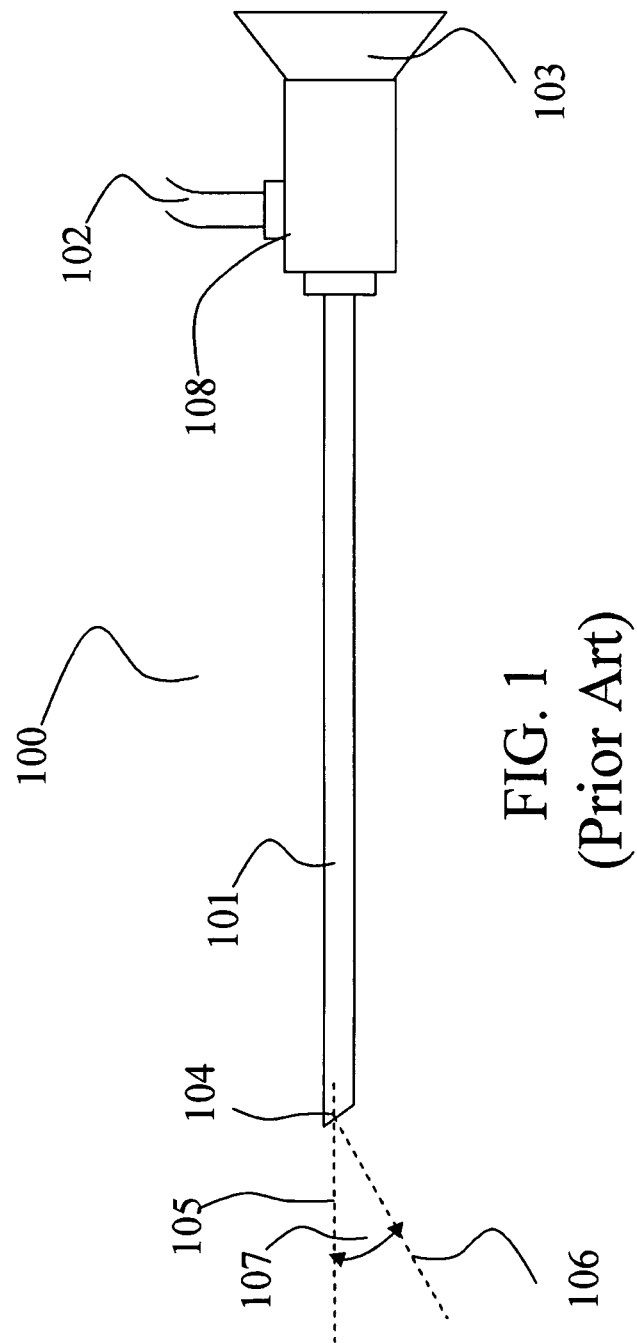
FIG. 1 illustrates a typical angled endoscope, with fiber optic light port for illumination, and an eye piece for viewing.
Figure 2:
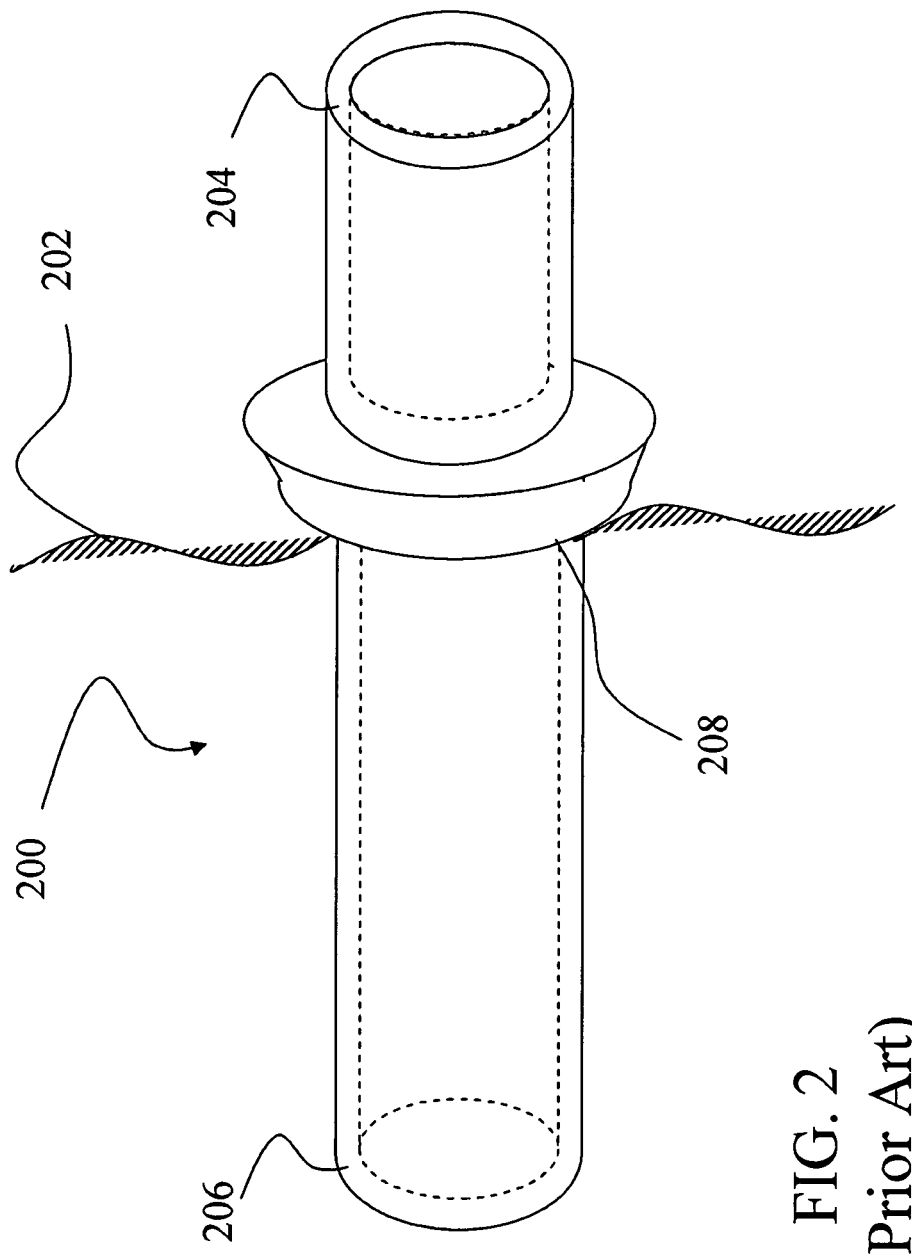
FIG. 2 illustrates a cannula inserted into a body cavity.
Figure 3:
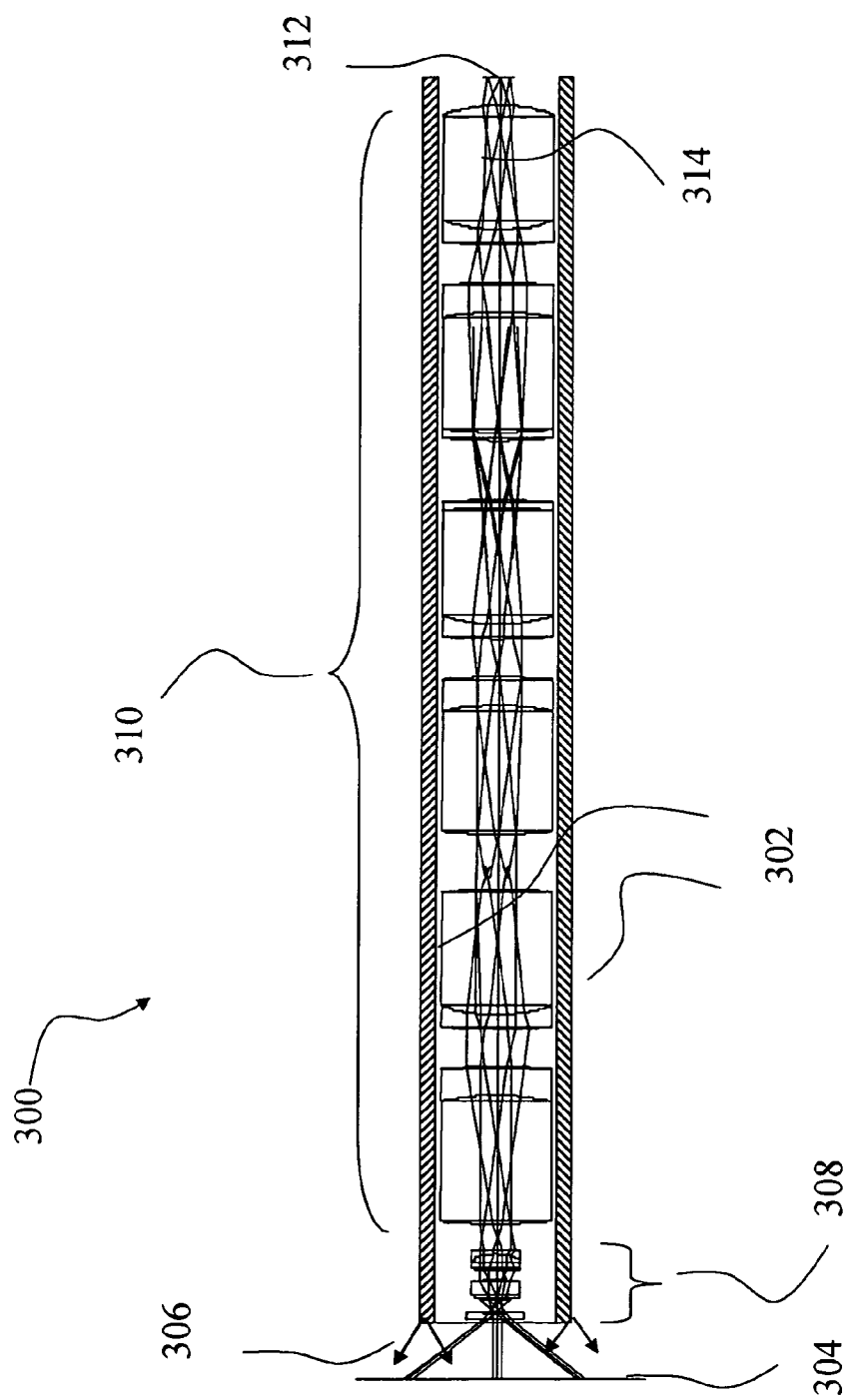
FIG. 3 illustrates a cross-sectional view of a typical zero degree, rigid endoscope with associated terrain for relay of the image through the length of the endoscope.
Figure 4:
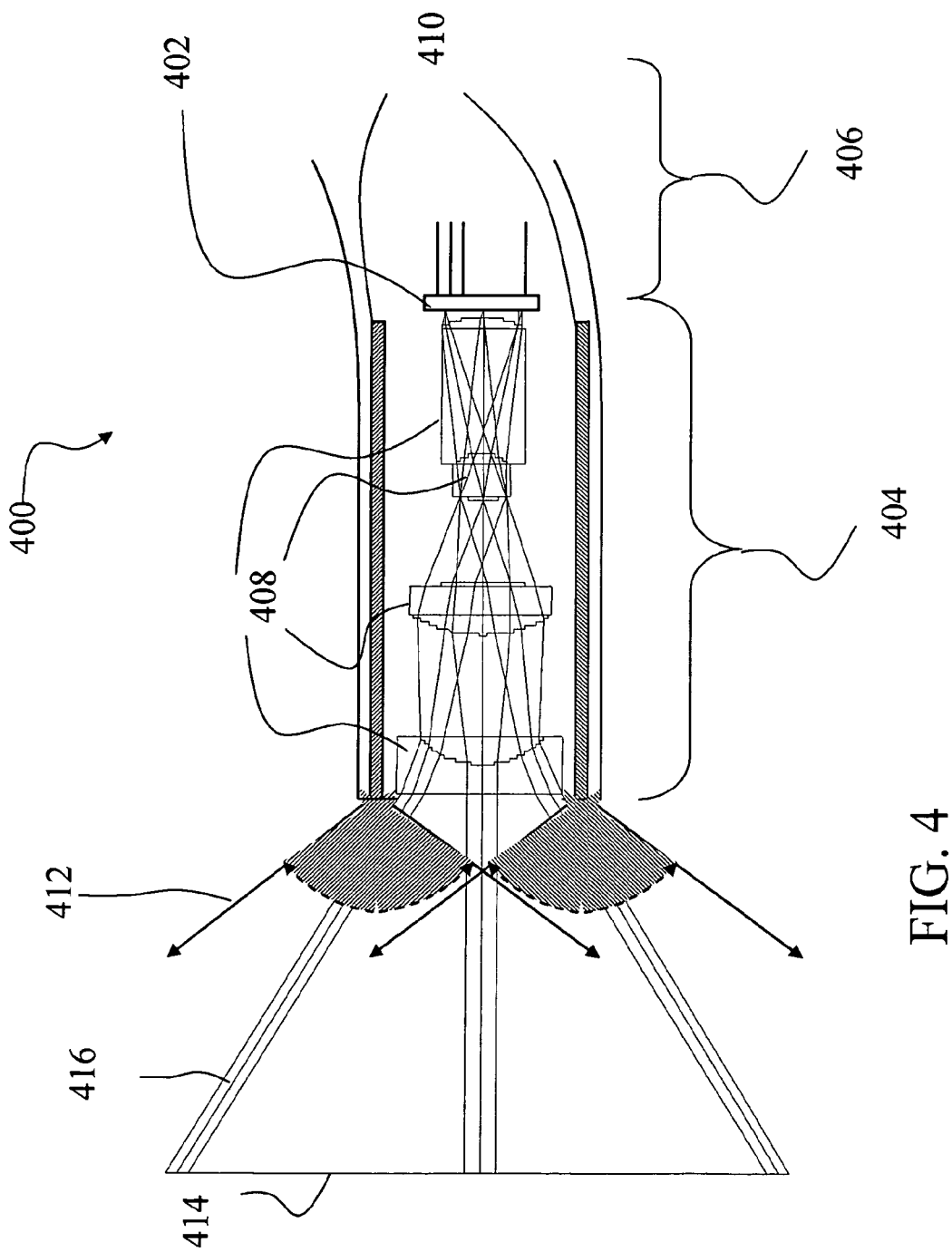
FIG. 4 illustrates a cross-sectional view of a zero degree typical flexible endoscope body (Chip on the Stick) with fiber optics illumination.
Figure 5:
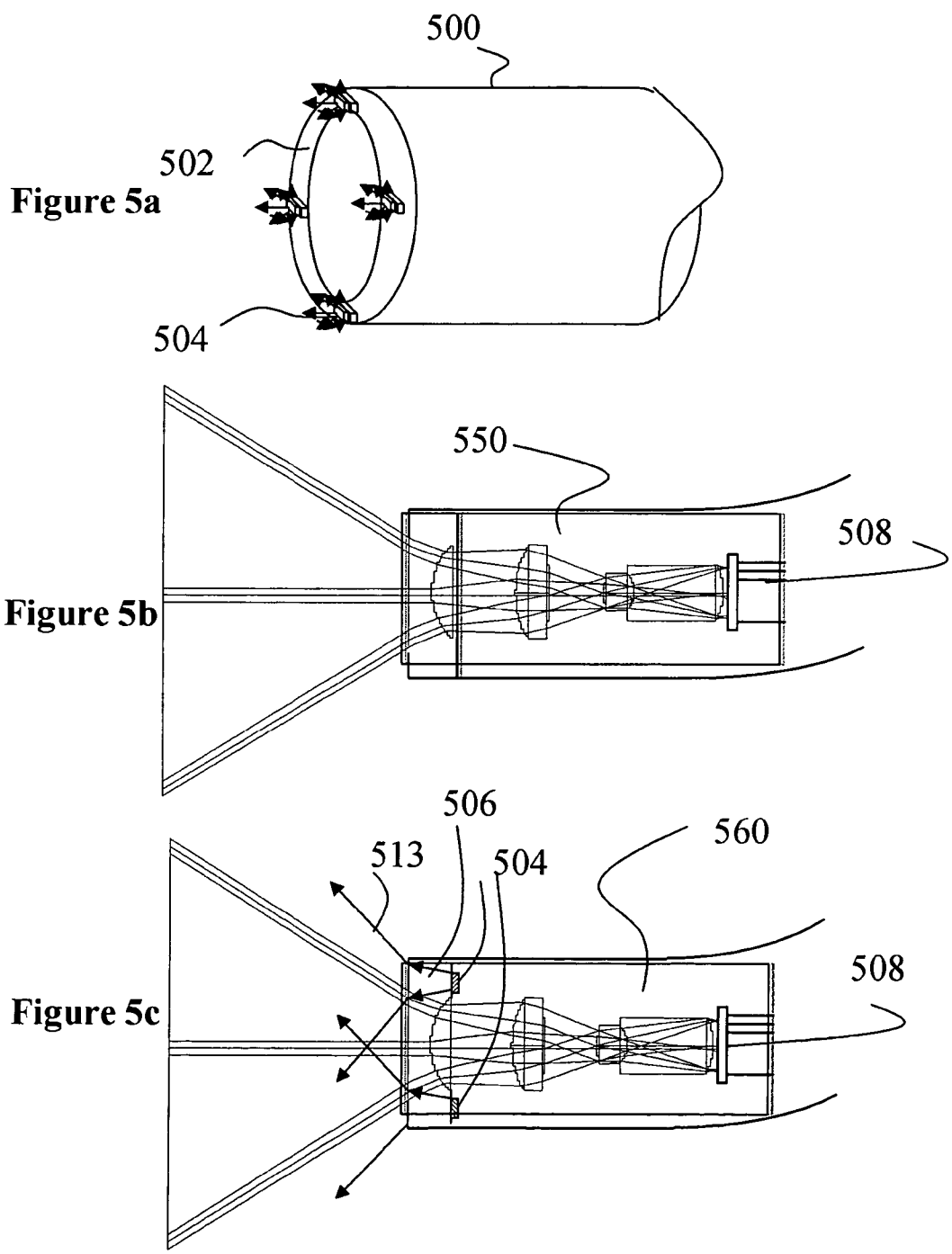
FIG. 5a illustrates LED illumination at the distal end of a disposable endoscope or cannula body.
FIG. 5b illustrates an OE Vision module plugged into the distal end of a flexible endoscope.
FIG. 5c illustrates fixed LED illuminators assembled behind the first negative lens of an OE Vision Module, used as a window at the distal end of a flexible endoscope.

FIG. 5a shows an array of LED illuminators 504 distributed at the distal end 502 of disposable endoscope or cannula body 500. Electrical drive currents for the LEDs and means of heat transfer using highly conductive material or micro heat pipes, to transfer the heat from LEDs to the proximal end of the endoscope or cannula body, can be provided within the body of the device. FIG. 5b represents a pluggable OE vision module 550 that can be attached to the distal end of an endoscope 400.

In another embodiment of a solid state illumination within the pluggable OE vision module 550, FIG. 5c illustrates the incorporation of white, color LEDs or lasers, IR or UV solid state light sources 504 behind the first negative lens 506 of the objective lens. This portion of the objective lens in effect acts as a window for the illumination source 504, since the concave portion of the first negative lens of the objective, is typically much smaller than the distal window of the scope. Solid state illumination sources in this configuration can be directly mounted to this glass window around the concave area of the lens. As the illumination light leaves the glass at the distal end, the angular radiation pattern 513 of the light expands as illumination is emitted outside the glass. Refractive, polarization, or wave-plates can also be implemented in the area of the negative lens beyond the concave portion to modify the illumination characteristic.

Removable and pluggable OE illumination and vision modules with protective disposable cover, or in a single use disposable medical device, can enable numerous advantages as well. For instance, the disposable medical device housing the OE module in a fully sealed sterile cavity, can be disposed of after removal of the pluggable OE module, where the protected EO module can now be plugged into a new sterile single use medical device housing for subsequent use, thereby eliminating the likelihood of contaminating body cavities in which the disposable medical devices are used.

Same type of removable and pluggable OE vision modules can be plugged into various designs of single use medical devices allowing for low cost variations in the medical device design and its functionality. The OE vision modules covered with single use protective cover that is fully sealed can be plugged into the distal tip of various medical devices, where the protective cover can be disposed of after use and a new protective cover seals and protects the OE vision module for subsequent use.

Different OE vision modules, with various functionalities can also be plugged into the same type medical device depending on the procedure to be performed, providing means to choose from a variety of application specific medical vision capability. For instance, white light illumination or multi-spectral visible OE modules can be used for traditional imaging in the visible range.

A pluggable OE module with additional deep blue or UV illumination could be used to induce bio-fluorescence inside the body and detect spectral emission from the object, at the same time as the visible imaging, to gain further information regarding the object, such as the tissue type and identifying lesions. An IR illumination can be used in the OE vision module, to image inside tissue or through scattering substances or fluids, to give additional in depth view. Different UV, visible and IR wavelength illumination with varying penetration depths can be used for depth dependent imaging inside the tissue. Various spectral component captured 2D images can subsequently processed and put together to reconstruct a 3D view of inside the body.

Use of such removable and pluggable OE illumination and vision systems inside a cavity in the body replaces a variety of conventional instruments otherwise needed for the same purpose, such as an external light source, fiber light guides, means of transmitting the light to the desired object, imaging optics, and/or electronic cameras. Further, the removable and pluggable OE systems according to some embodiments of the invention can be used to perform tissue analysis inside the body, thereby eliminating the need for taking tissue for biopsy, and then performing a biopsy on dead tissue. This enables in vivo tissue analysis without the delay typically required to obtain a biopsy report, and further allows for real-time surgical procedures to be performed instead of possible follow-on surgical procedures after review of biopsy reports.

As mentioned above, LED sources and other solid state light sources such as Vertical Cavity Surface Emitting Lasers (VCSELs) can be used for illumination as stand-alone removable LED illuminators or as illuminators within a removable and pluggable OE illumination and vision module. The use of LEDs and other solid state sources can have several advantages over conventional external white light sources. With an LED-based illumination, a true, visible light source with no IR content is available for the endoscopic application, allowing imaging of the object in the visible region with custom made spectral illumination that is obtained from the spectral range of each LED used in the illumination. The specific color component of each LED can be used independently or in conjunction with each other to realize a tunable spectral illumination in a specific range of the visible spectrum. Use of LED sources within the body of a disposable medical device or within a removable pluggable OE illumination and vision module, also eliminates the need for fiber optic illumination bundles for delivery of light and inside the scopes. The extra room provided due to the elimination of the illumination fibers can make the endoscopes and other medical devices incorporating the LED sources, smaller in size and more flexible and maneuverable inside the body.

LED sources can provide illumination in a wide range of the electromagnetic spectrum, from UV, to visible and IR, where the individual LEDs in a specific spectral range can be independently controlled in time and the corresponding images independently processed based on individual captured frames. Each LED spectral component can be independently designed in the LED, or obtained with independent processing of each LED spectrum, via secondary photo-luminescence process on blue or UV LEDs, or using edge or band pass spectral color filters such as multilayer dielectric optical filter coatings. For imaging in the visible region, Red, Green, and Blue LEDs in primary colors can be used with or without other non-primary colors such as amber or cyan where the multiple spectral LEDs together form a white illumination.

Figure 6:
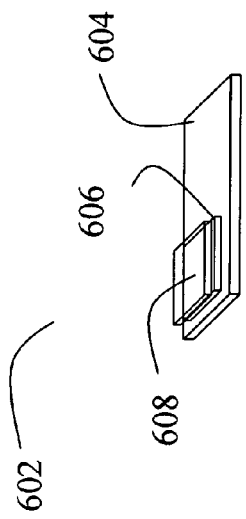
FIG. 6 illustrates one embodiment of a phosphor-converted LED.

Phosphor-converted LEDs can provide white output or a specific range of colors in the visible band where the spectral output can be further modified with a specific edge filter or band stop or band pass filter coating. For instance, FIG. 6 illustrates one embodiment of a phosphor converted LED 602 comprising a LED substrate 604, an LED 606, and a phosphor conversion material or optical thin film filter 608. The phosphor conversion material or optical thin film filter 608 converts a portion of the primary emission of the LED 606 to longer wavelengths. The longer wavelengths combine with an unconverted portion of the primary emission to produce white light or a specific range of colors.

By using multiple color LEDs and synchronizing a black and white image capture device to grab the synchronized color component images, the use of color camera chips or high resolution 3 CCD or 3 CMOS imaging devices are eliminated. In this case, a single CCD or CMOS image capture device is used to capture the three or more images in a time synchronized fashion, where each color component image takes advantage of the full image capture device resolution by incorporating all the pixels in each color image component. Simple black and white image capture devices are also cheaper to use, especially compared to 3 chip image capture devices, where in effect the resolution of a synchronized black and white imaging CCD or CMOS using synchronized color illumination provided by the LEDs is equivalent to a same pixel 3 chip image capture device.

Using color synchronized image capture devices also allows the use of much higher resolution image capture devices in chip on the stick cameras where space is limited at the distal tip of the endoscope for the image capture device. A variety of illumination configurations are possible using LED chips, where the uniformity, angle and extent of the illumination are freely controlled by the positioning and design of the LED light sources. Various illumination configurations are disclosed more fully in U.S. patent application Ser. No. 11/233,684.

In current endoscopic imaging systems where a white light illuminator is used, the illumination spectrum is determined by the light source and the optical path the light is transmitted through before reaching the object inside the body. Subsequently, a 3-color image capture device (e.g., a single-chip RGB camera or 3-chip RGB camera) captures the reflected light from the object according to its RGB filter set and image capture device spectral sensitivity. An image display unit in turn displays the captured RGB image according to its own color filters.

With a disposable LED illumination or LED-based removable and pluggable OE vision system according to some embodiments of the invention, it is possible to match the RGB spectrum of the display device with the exact matching LED illumination spectrum. This allows for a "true color" imaging system from illumination all the way to the display output. Other LED spectral components can also be added to the illumination to display chain, where RGB amber, RGB cyan, and the like or any combination thereof are used to expand the color rendering and display capability of the complete vision system for a "true life color imaging" capability.

Infra Red (IR), Ultraviolet (UV) LEDs, or narrow spectral band VCSELs can be used based on their transmission characteristics in the medium of insertion, such as wavelength dependent penetration depth inside the medium or the effect they have on the object of interest (such as inducing autofluorescence). With an endoscope equipped with a full range of LED wavelengths, or a specific range of illumination wavelength, it is possible to obtain a full spectral image of the object by turning the various LEDs on and off at specified times, and in a controlled spectral range depending on application, while a time synchronized imaging process captures various spectral images based on the illumination at the time of capture. The LEDs can be distributed illuminators used with fixed image capture devices on the scope, introduced within the body of the disposable medical device as part of an OE vision module, or independently introduced inside the body with or without other medical devices.

Figure 7:
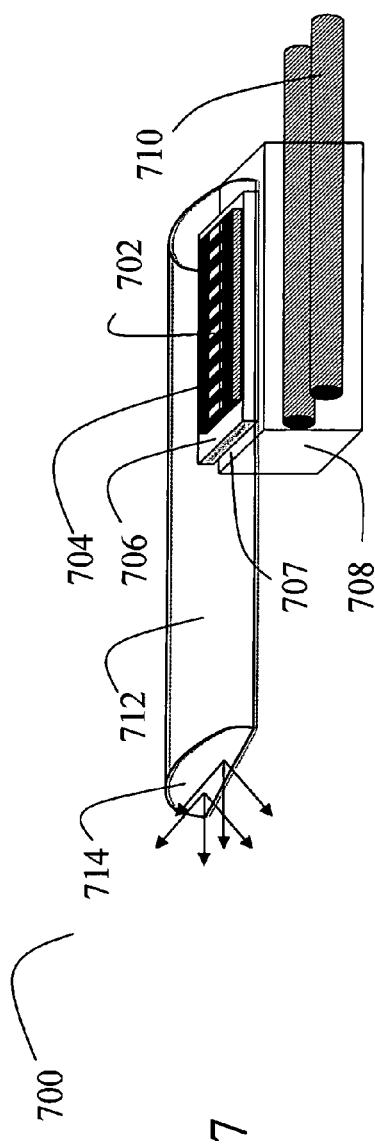
FIG. 7 illustrates light from an array of LED illuminators coupled into a sub-cylindrical shape light guide, where a heat slug under the LED array substrate is equipped with the ends of heat pipes.
Figure 8:
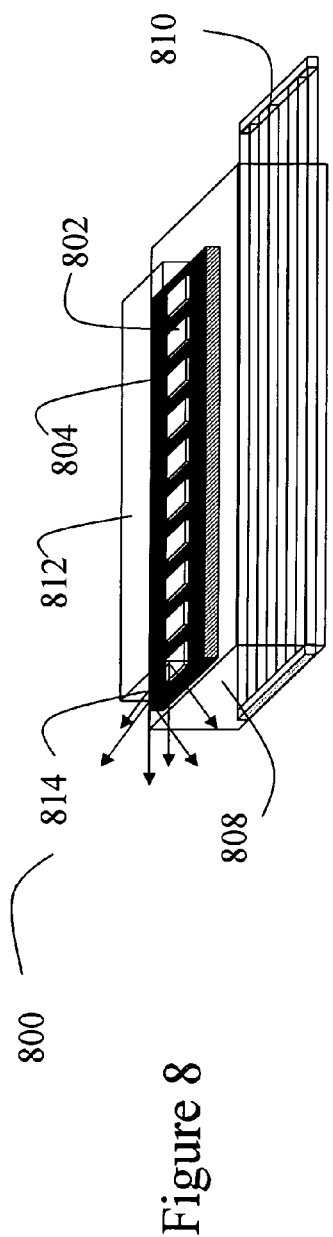
FIG. 8 illustrates light from an array of LED illuminators coupled into a long rectangular light guide, where a heat slug under the LED array substrate is equipped with micro-fluidic cooling channels.

An array of LED illuminators can have variety of spectral components or spectral bands incorporated in a single OE illuminator module. FIGS. 7 and 8 represent such arrays of LEDs 702 and 802 with different or similar spectral bandwidth mounted on a single substrate 704 and 804. In FIG. 7 the light from the LED array is coupled into a sub-cylindrical optical guide 712, where light from the LEDs is mixed through the guiding process as it traverses the length of the light guide. In FIG. 8 the LED light is coupled into a rectangular light guide 812. Light guides 712 and 812 have highly reflective specular (Silver) coating, or diffuse (thick TiO2) coating on all sides except at the LED input area and the output surface 714 and 814 respectively. Light guide output surface 714 and 814 can have micro surface features or can be roughened, to aid efficient light extraction from the light guide into air.

Substrate 704 may be attached to the LED thermal base (ceramic or multilayer structure) 706 using highly conductive solder which in turn makes intimate thermal contact with the heat slug 708. The thermal contact in joint 707 between the LED thermal base 706 and heat slug 708 is aided by thermal paste, gel or highly conductive epoxy. Mechanical pressure can also be exerted on this thermal joint to guarantee absence of any air bubbles between the two thermal surfaces at joint 707. The heat slug 708 can be a copper block equipped with heat pipes within its body to efficiently transfer heat away from the LEDs to an appropriate distance. In FIG. 8 the LED substrate is directly attached to the heat slug body 808, which is alternatively equipped with micro-fluidic cooling channels 810. Fluid source with adequate pressure and flow speed is provided to these micro-fluidic, heat transfer block 808 to transfer heat away from the LEDs.

LED, image sensor and other electronic lifetimes are more than order of magnitude longer than bulb type light sources (50 k hours depending on the drive condition). The long life time in conjunction with the reliability associated with these OE devices, and capability of thorough testing of the OE in between the removal and plug-in process into the medical device, allows for reliable multiple use of OE illumination and vision modules inside medical devices in especially surgical procedures, where dependable illumination and vision system is one of the most critical parts of the system.

LED power consumption is also much lower than high power light sources. Consequently, removable and pluggable OE modules are very efficient since there is no need for i) transferring light from the source through fiber optic light guides, ii) coupling the light into the scope light guides, or iii) transmitting through the fiber optic light guides through bends in the fiber. Light powers in the order of 1000 lumens are in fact possible with use of only a few high power LEDs. Thus, simple low power electrical connections to the LED illuminators and OE module, containing image sensor and electronics can be provided through the single use disposable medical device.

Further, LEDs are robust, and do not break, unlike fiber optic light guides. This allows for ease of installation of LEDs and OE vision modules on virtually any device used in surgery or for other borescopic purposes. OE illumination and Vision modules can be exposed, touched, installed, removed and reinstalled easily in many shapes and forms to any electromechanical body without complication.

LEDs do not produce any electromagnetic interference, thus eliminating the need for complicated EMI management systems such as Faraday caging around the OE modules. Because of size, reliability and safety of LEDs, these light sources are ideal choice for "in location" illumination of the object inside the body. In this case, only electrical power is transmitted to the light sources inside the body along with possible electrical control signals.

By eliminating conventional fiber optic illumination guides inside the endoscope body, there is more space for the OE vision module, where the size directly relates to the image information capture as well as information transfer capability of the system. With more space available to the imaging optics, larger diameter optics, multiple imaging optics, or optics with higher level of functionality as well as higher resolution and higher performance image capture devices can be used, making larger image FOVs and higher resolution possible.

LEDs do not require a warm-up procedure. LEDs are capable of providing instant illumination with the exact color point at initiation. Optical power and color maintenance over the life time of the LED are also critical features of solid state light sources.

LED illumination systems or removable and pluggable OE illumination and vision modules are modular, where one or multiple OE modules can be inserted into the body independent of one another, via separate medical device bodies, at the distal end of an endoscope, or incorporated at convenient and efficient locations on surgical tool tips or disposable cannulas, or other single use access devices such as Ear Nose Throat (ENT) speculum or cannula, providing an always sterile illumination and visualization of site inside the body. These single use medical devices incorporating the OE illumination and vision system could be battery operated or take power through the medical device that is plugged in externally.

One type of an embodiment of an LED illuminated disposable cannula 200 and disposable ENT speculum 900 is illustrated in FIGS. 9a through 9d. Speculum 900 makes contact to the natural body orifice beyond the skin 903, making contact with the body at the opening of the orifice 908. In this exemplary embodiment, the body of the cannula or speculum which is clear to the light in the visible spectrum is completely lit by white or color LEDs 902 mounted at the proximal end 204 of the cannula or proximal end 904 of the speculum. Electrical power to the LEDs is provided by power connection 905. As illustrated in FIG. 9a and 9b, the LED light fed into the cannula or speculum body goes through Total Internal Reflection (TIR) 907 or is reflected by high reflective coating on the surface of the cannula 200, or speculum 900 as it travels the length of the cannula or speculum to the distal end 206 and 906 of cannula and speculum respectively, at which point the light leaves the cannula or speculum illuminating the site inside the body and tools as indicated by radiation pattern 910. As mentioned before the distal surface 206 or 906 of cannula or speculum acting as light guide could be roughened to achieve better extraction from the light guiding body.

Figure 10A:
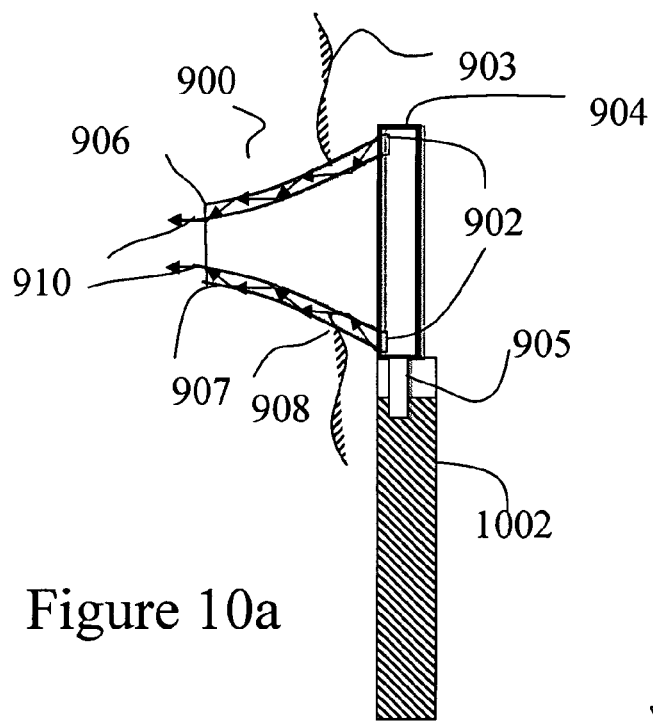
FIG. 10a illustrates an illuminated speculum on a powered handle.
Figure 10B:
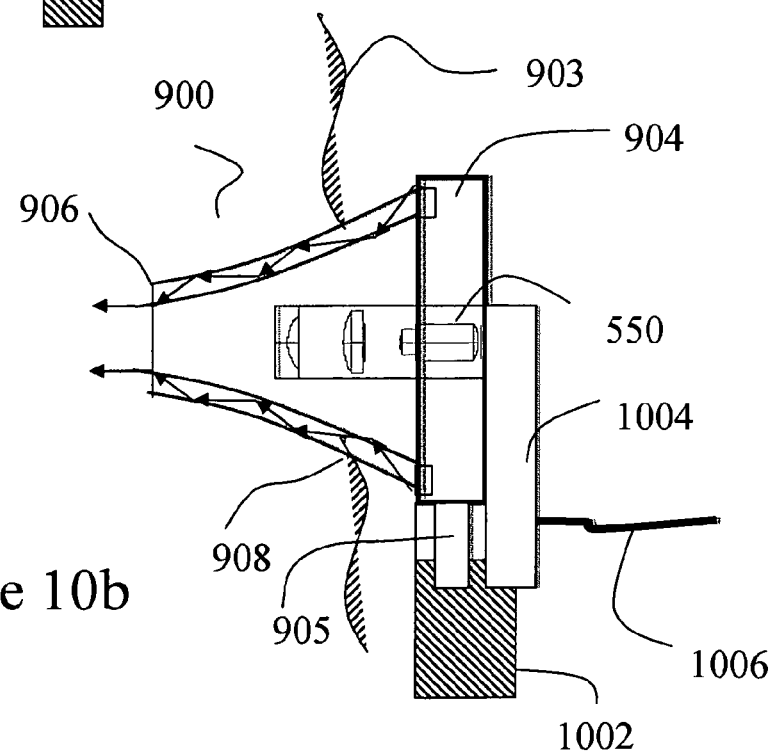
FIG. 10b illustrates an OE vision module plugged into the illuminated speculum.

FIG. 10a illustrates the speculum in FIG. 9d as it is plugged into a handle 1002, where power connection 905 draws power from batteries in the handle 1002, or external power provided to the handle by a power cable. FIG. 10b illustrates further incorporation of a separate pluggable OE vision module 550 on the lighted speculum 900 and handle 1002. The OE vision module 550 is connected to the handle by structure 1004 which caries power to the OE vision module and transfers image data from the sensor to video cable 1006. Video cable 1006 could also provide external power to the complete otoscope unit consisting of handle 1002, lighted speculum 900, and OE vision module 550.

Figure 10C:
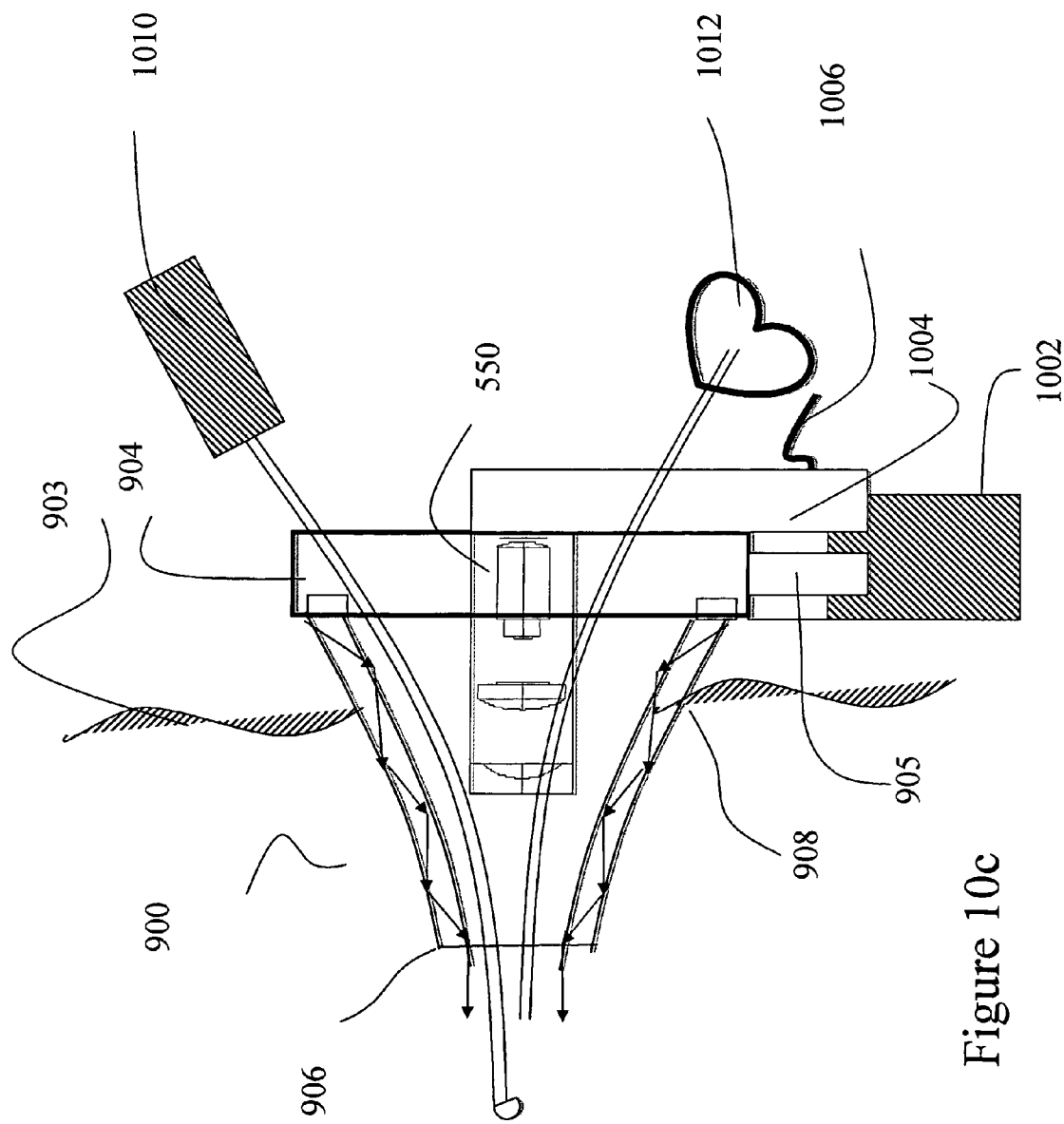
FIG. 10c illustrates the OE vision enabled, lighted speculum of FIG. 10b, with various medical tools inserted into the body.

By mounting the OE vision module 550 on structure 1004, the rest of the opening in proximal end 904 may remain free for access to inside the body 903 through the speculum. For example if the speculum is used to visualize and gain access into the ear canal, the examiner can use tool 1010 to remove earwax (cerumen) or use tool 1012 to puff air into the ear testing the mobility of tympanic membrane, as illustrated in FIG. 10c.

Removable and pluggable OE vision modules containing LED illumination can be plugged into variety of single use disposable endoscope, surgical medical device bodies, used in a fixed position with respect to the medical device body, or deployed out of the medical device body once the medical device distal end is inside the body. Through the deployment process of the OE illumination and vision modules, that are plugged into the distal tip of the medical device, the OE module can position itself outside the normal medical device volume, creating space inside the medical device and enabling further tool insertion through the cavity that the OE module was stored in during the insertion of the medical device into the body, thus allowing for further medical device functionality.

As an example of another fixed pluggable OE vision module within the housing of a single use medical device, FIG. 11a depicts a laryngoscope 1100 with a handle 1102 containing batteries for power, and a disposable curved Macintosh type blade 1104, that can be used for manual visualization of the laynx used in standard tracheal intubation. FIG. 11b illustrates incorporation of the pluggable OE illumination and vision module 1106, as it's plugged into a fully sealed housing inside a disposable blade of the Laryngoscope 1104. A molded optically transparent window 1108 in front of the blade provides optical access for illumination light and provides wide access FOV for visualization. Window 1108 can also be used as the opening to inside the disposable blade for plugging in and removing the OE illumination and vision module 1106. Once the OE illumination and vision module 1106 is plugged in and operational, the access window is then sealed in place using appropriate medical grade epoxy under relative vacuum, to avoid any moisture getting trapped inside the disposable blade 1104 and OE module 1106 cavity. Certain moisture absorbing beads could also be housed in the blade 1104 and OE illumination and vision module 1106 cavity to assure dry air inside the sealed housing.

Thermal pads 1114 on top and bottom of the OE illumination and vision module 1106 are used to make close contact with the top and bottom surfaces of the OE module and in turn an illumination LED heat sink, for efficient transfer of heat from the LED module to the window 1108. The OE illumination and vision module connector portion 1110 includes electrical connections configured to mate with corresponding electrical lines 1112 that run through the laryngoscope blade 1104 to the laryngoscope handle 1102.

FIG. 12a shows a front view of the pluggable OE illumination and vision module 1106 used in the disposable blade 1104 of the laryngoscope 1100. The pluggable OE illumination and vision module 1106, is fully housed in it's own housing 1208, with an optical window 1206 to allow illumination light to pass through and the image capture light to transmit inside the OE module 1106. The vision module 550 is positioned in the middle of dual lensed LED illuminators 1204. The heat from the LED illuminators 1204 is conducted by the LED heatsink to the OE module body 1208 and OE module window 1206, as well as coupled through laryngoscope blade 1104 heat conducting pads 1114 to the external window 1108 on the blade, to keep both windows warm up avoid condensation and fogging during use. The OE module 1106 can be turned on a short while before the procedure to warm up the windows if the laryngoscope blade 1104 is stored in a cold environment.

Figure 12B:
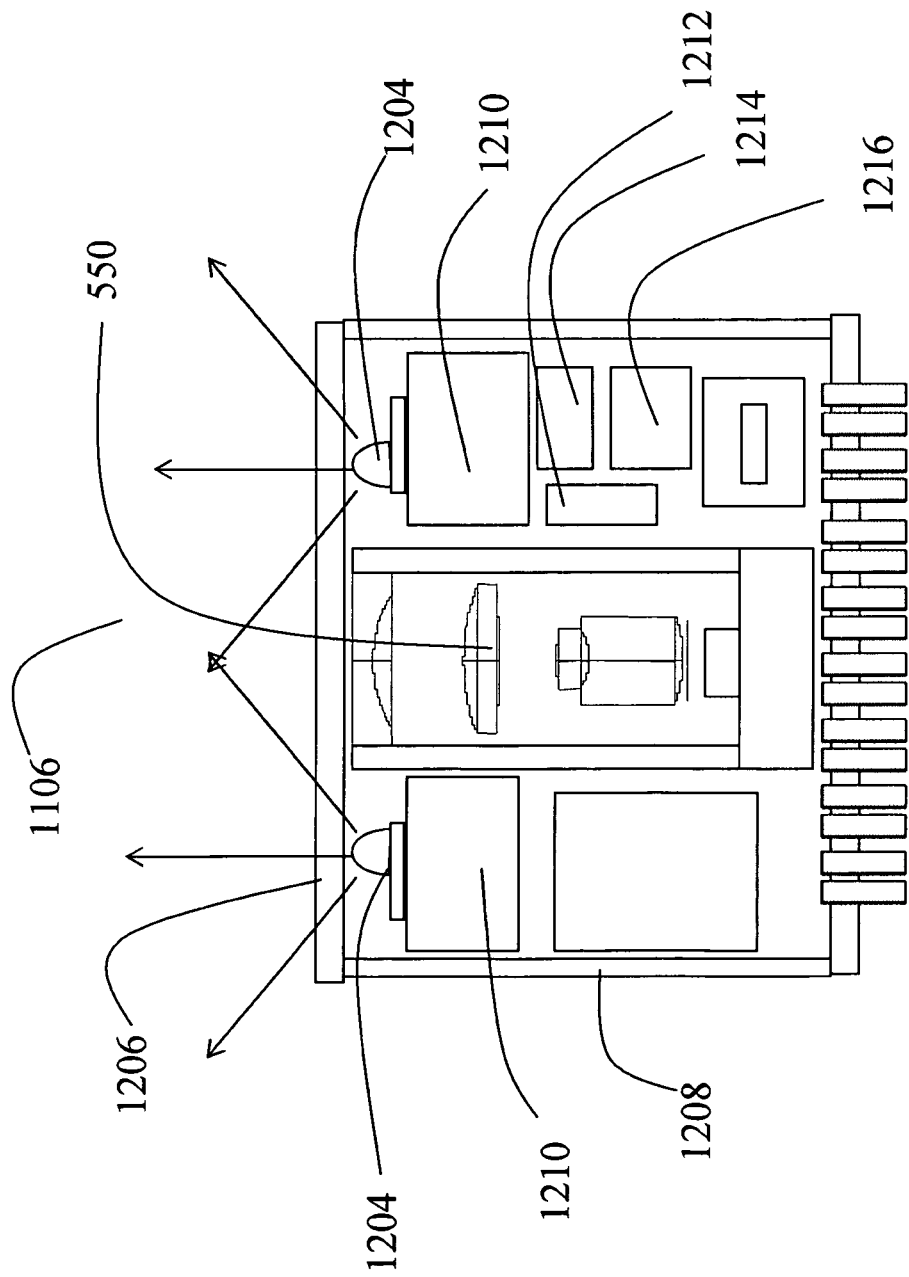
FIG. 12b illustrates a top view of the OE illumination and vision module incorporated inside the visual laryngoscope blade depicted in FIG. 11b, with associated electronics for image processing and image transfer.

FIG. 12b illustrates a top view of the OE illumination and vision module 1106 used in the laryngoscope blade 1104, where various electronic components 1212, 1214, and 1216, used for driving the LED illuminators 1204, and image processing of the captured images from imaging module 550, are also contained in the in the OE module housing 1208. LED illuminator 1204, and heat sinks 1210 are used to conduct heat to the laryngoscope blade heat conducting pads 1114 on top and bottom of the OE module 1106, as mentioned before.

Various electrical 1302, optical 1304, and wireless 1306 connections to the OE illumination and vision module 1106 are represented in FIGS. 13a-13d. The optical connection 1304, can be used for high bandwidth digital imaging sensor or sensors used within the OE vision module 1106. 1304 is an optical transmitter that can multiplex digital image data from a digital image sensor or multiple digital image sensors, into a serial digital input modulating an optical source such as a high speed LED or a VCSEL 1310 depicted in FIG. 13b. The modulated light from optical transmitter source high speed LED or VCSEL 1310 is then coupled, with or without a coupling lens in transmitter modules 1304a and 1304b respectively, into multimode fiber optic 1308 transmission line. The fiber optic transmission line could be routed through the blade to a multimode fiber connector on the blade or the handle, where an external fiber optic transmission line transmits the high bandwidth, high speed image information to an optical receiver in the display unit. Alternatively the multiplexed digital data can be transmitted wirelessly to a wireless receiver in the display unit, via wireless connection 1306.

Figure 13A:
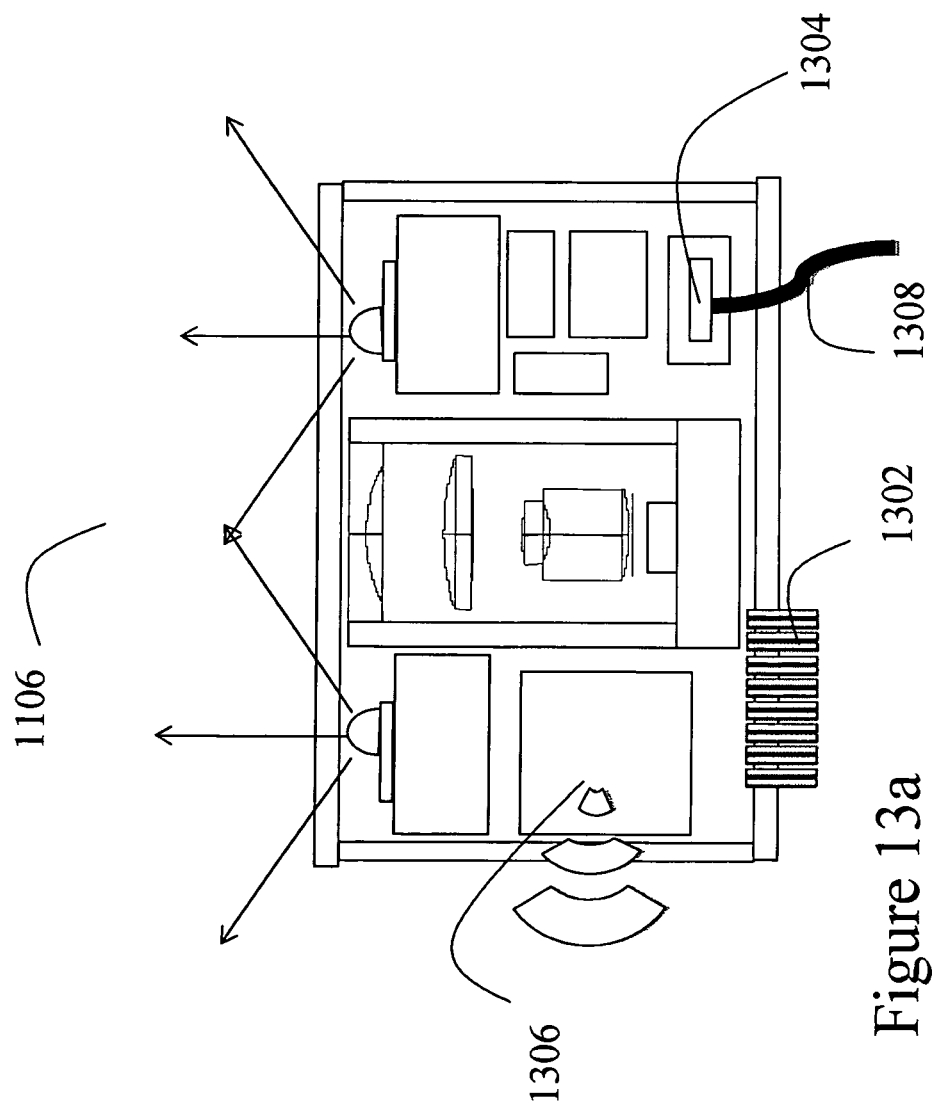
FIG. 13a illustrates various electrical, optical and wireless, connection to the OE illumination and vision module plugged into an endoscope body.
Figure 13B:
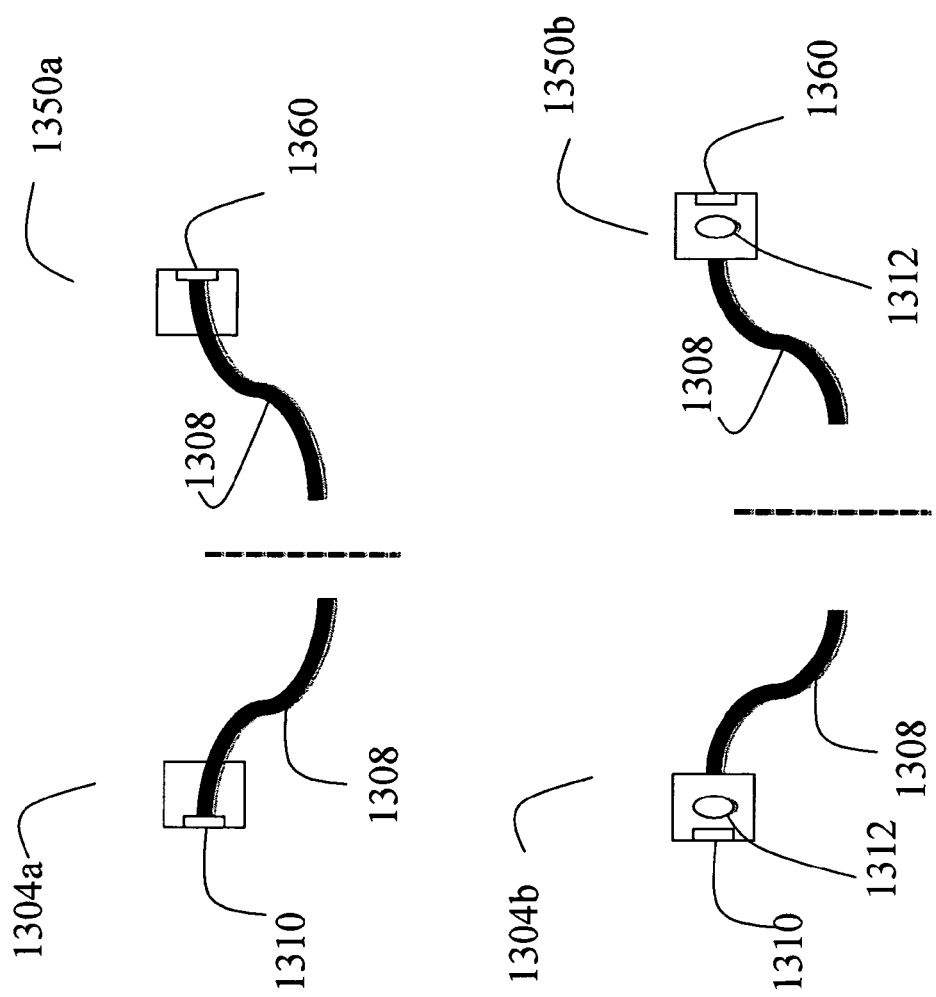

FIGS. 13b, 13c and 13d illustrate basic optical transmission link from OE vision module to the display unit. FIG. 13b illustrates a one way connection between the OE vision module 1304a and 1304b, to the display unit, where VCSEL 1310 is butt coupled into the multi-mode fiber 1308 in 1304a, or focused by a coupling lens 1312 into multi-mode fiber 1308 in 1304b. On the display side the multi-mode fiber can also be butt coupled into a high speed detector in 1350a, or focused on the high speed detector by a 1312 coupling lens in 1350b.

FIG. 13c represents a two way optical link from the OE illumination and vision module 1304c, to the display and control unit 1350c. Different transmission wavelengths can be used for the two way transmission through the same multimode fiber link 1308. Dichroic beam splitters 1314 are used on OE module 1304c, as well as the 1350c display and control side to separate the transmit and receive signals accordingly. While VCSEL 1310a with wavelength #1 transmits the image data upstream to the display and control unit 1350c, as control unit 1350c uses the dichroic beam splitter to direct wavelength #1 to high speed data detector 1360. VCSEL 1370 on the control and display unit 1350c sends control signals in wavelength #2, where it's reflected by the dichroic 1314, and launched into the fiber link downstream to the OE module 1304c, where the dichroic beam splitter 1314 reflects the control signal wavelength #2 to the high speed detector 1320 in OE module 1304c.

FIG. 13d, represents a 3 way transmission link with 3 different wavelengths between the OE module 1304d and control and display unit 1350d. The first two communication links work the same as two way communication with wavelength #1 and #2 between OE module 1304c and control and display unit 1350c. The third transmit line using wavelength #3 could be used in the OE module 1304d, to gain extra bandwidth to support higher transmission or with added image sensors in the OE module. Philips type 3 way dichroic beam splitters 1316 are used in this case to separate the 3$^3$rd wavelength. VCSEL 1330 in this case transmits wavelength #3, where it's reflected by Philips dichroic prism 1316 on OE module 1304d, and coupled upstream to display and control unit 1350d. Philips dichroic prism 1316 reflects wavelength #3 in display and control unit 1350d, towards high speed detector 1380.

Incorporating solid state OE illumination and vision modules in endoscope and surgical device bodies provides a desirable cost advantage over conventional lamp and fiber guide systems, as it replaces the expensive light sources, long fiber optic light guides to transfer illumination light from the light source to the scope, and the illumination light guides inside the scope as well. Low level power is needed for the LED light sources, image sensors and drive electronics, thus the electrical connection of the OE illumination and vision module is also much easier.

Only electrical power and LED control signals need to be provided for the endoscope, eliminating the heavy and bulky fiber optics illumination cable connection to the scope, increasing the maneuverability and durability of the endoscope. OE illumination and vision modules are also more robust to shock and vibrations or extreme environmental conditions than fiber optic illumination and external camera systems.

In addition to the above exemplary embodiments in FIGS. 9a-11b where the LED illuminators are used in fixed positions within the endoscope body, or embodiments where the OE vision modules are used in fixed position within the endoscope body or cannula body, other deployable embodiments are possible for more effective illumination and imaging of the surgical site. In these deployable embodiments, the OE illumination and vision modules are deployable from an insertion position in which they are held within the insertion body or within a close profile of the insertion body, to an operational position where they are conveniently pointed to an object of interest. In operational position, the illumination light as well as the imaging FOV can be directed to the surgical site from beyond the endoscope body, where deployment of the OE module holding structure positions the vision module off axis from the axis of the insertion body, possibly increasing the functionality of the surgical device as well.

FIGS. 14a and 14b illustrate a pluggable OE illumination and vision module 1400 being connected to the distal tip of a rigid endoscope 1401. OE module 1400 consists of illumination 700 depicted in FIG. 7, and vision module 550 depicted in FIG. 5b. Heat slug 1408 equipped with heat pipes 1410 is provided by the rigid endoscope 1401. When the OE vision module is plugged into the distal tip of the rigid endoscope 1401, appropriate thermal gel or grease is used to have the LED thermal base 706 under the LED substrate 704, make intimate and effective thermal connection with heat slug 1408. Electrical connections 1412 are made to the OE module 1400 as it's plugged into the rigid endoscope body 1401, for power and drive input and image data output. As described in FIG. 7, the LED array 702 illuminator light is coupled to light guide 712 and transmitted to the tip of the OE module 714.

Figure 15A:
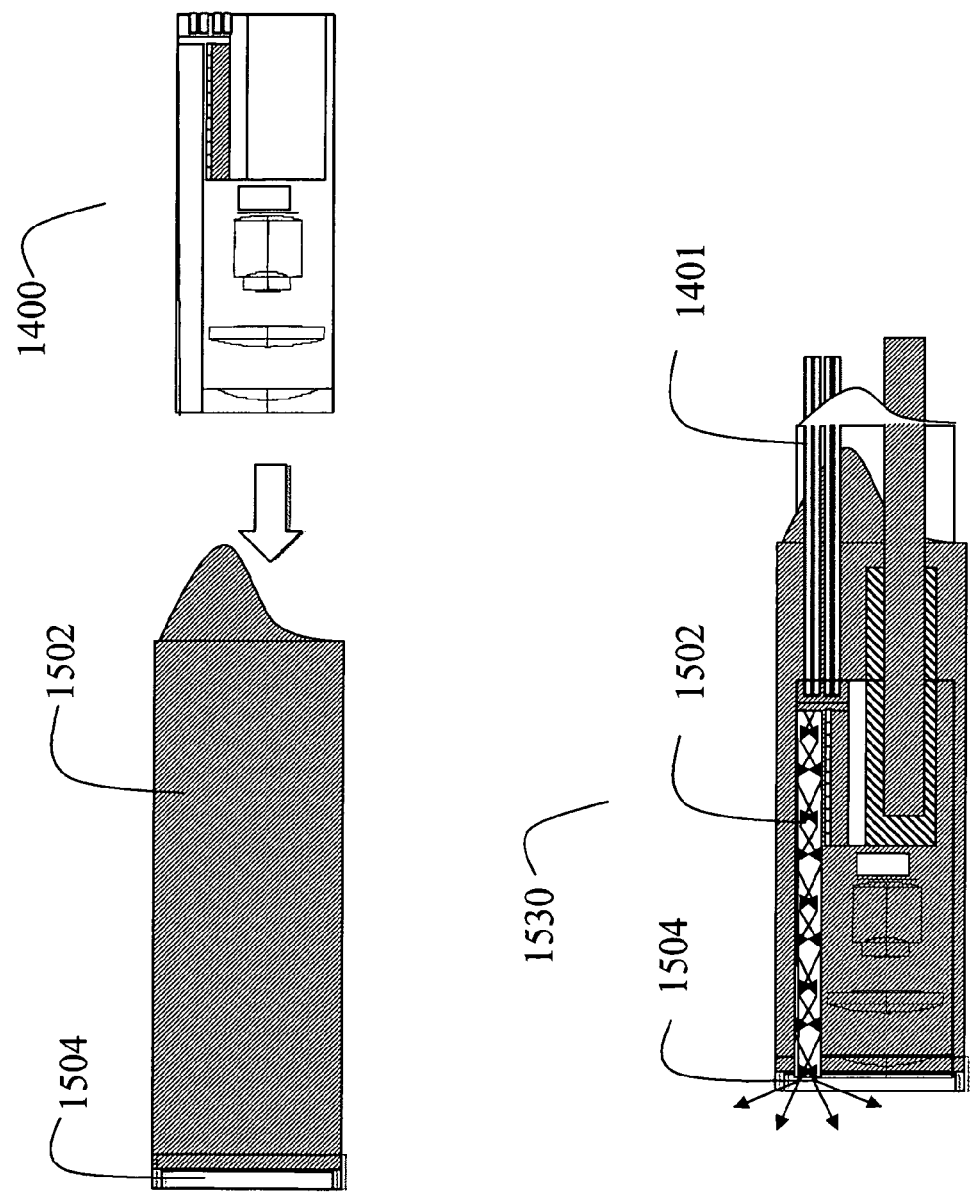
FIGS. 15a and 15b illustrate the pluggable cylindrical shape OE illumination and vision module depicted in FIG. 14a, being inserted into a cylindrical protective cover with a flat (FIG. 15a) or hemispherical (FIG. 15b) optically transparent window.

FIG. 15a represents OE illumination and vision module 1400 being inserted in a single use protective cover 1502, with a flat distal optical window 1504 sealed in the housing. Windowed protective cover 1502 can be disposed off, after each use and the OE module 1400 can be unplugged from the rigid endoscope 1401 for subsequent use.

Figure 15B:
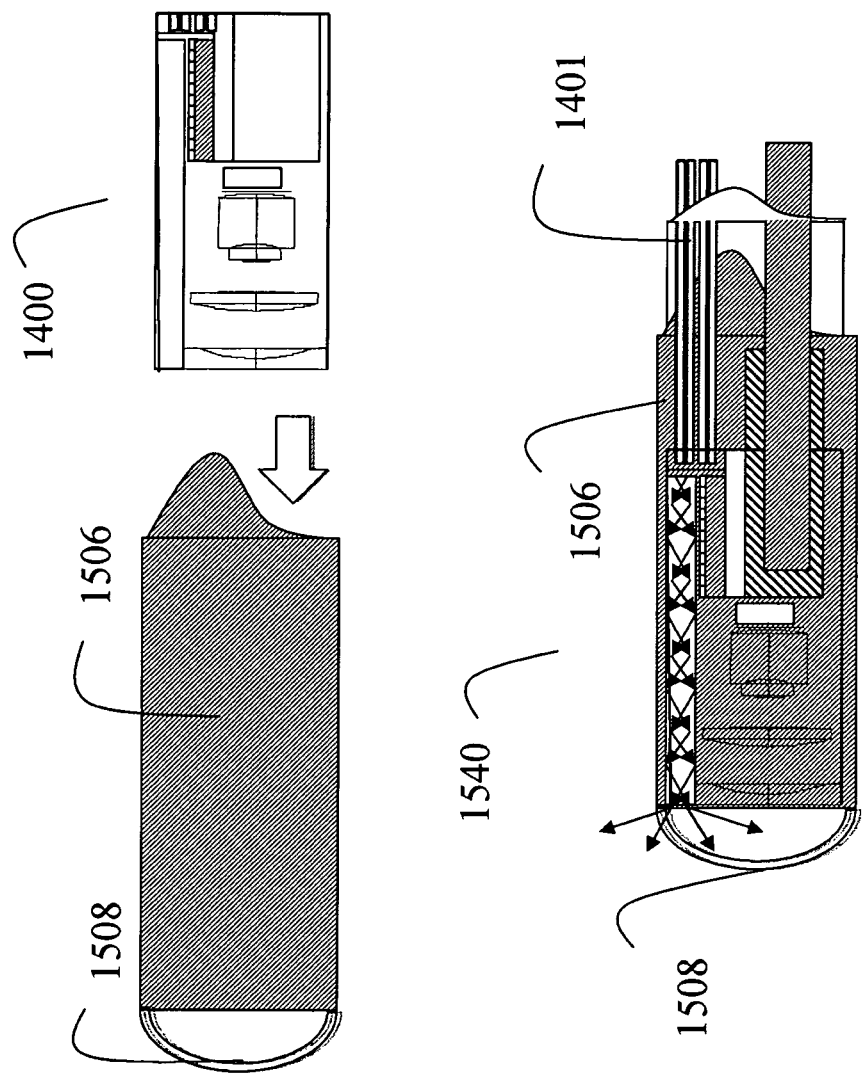

FIG. 15b illustrates OE illumination and vision module 1400 being inserted in a single use protective cover 1506, equipped with a fully sealed hemispherical window 1508.

FIG. 15c illustrates the pluggable OE vision module 550 of FIG. 5b, being inserted in a single use protective cover 1510 with sealed hemispherical window 1512. The jacketed pluggable OE vision module 1550 can now be plugged into the distal tip of flexible endoscopes with appropriate electrical connection to the OE vision module through the flexible endoscope body.

Figure 15D:
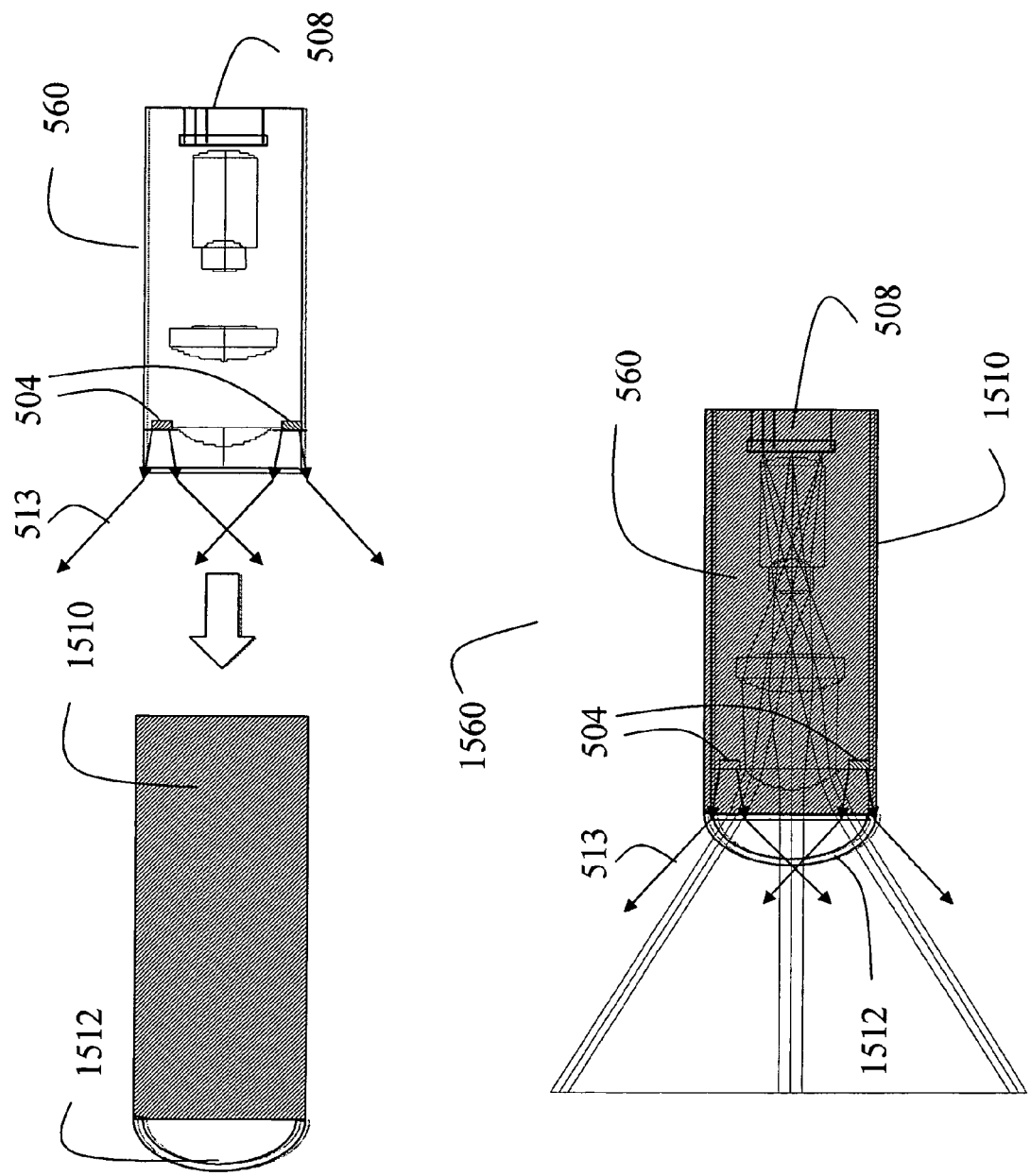
FIG. 15d illustrates the pluggable cylindrical shape OE vision module from FIG. 5c, being inserted into a cylindrical protective cover with a hemispherical optically transparent window.

FIG. 15d illustrates OE illumination and vision module 560 of FIG. 5c, being inserted into the same single use protective cover 1510 of FIG. 15c, with hemispherical window 1512.

Figure 15E:
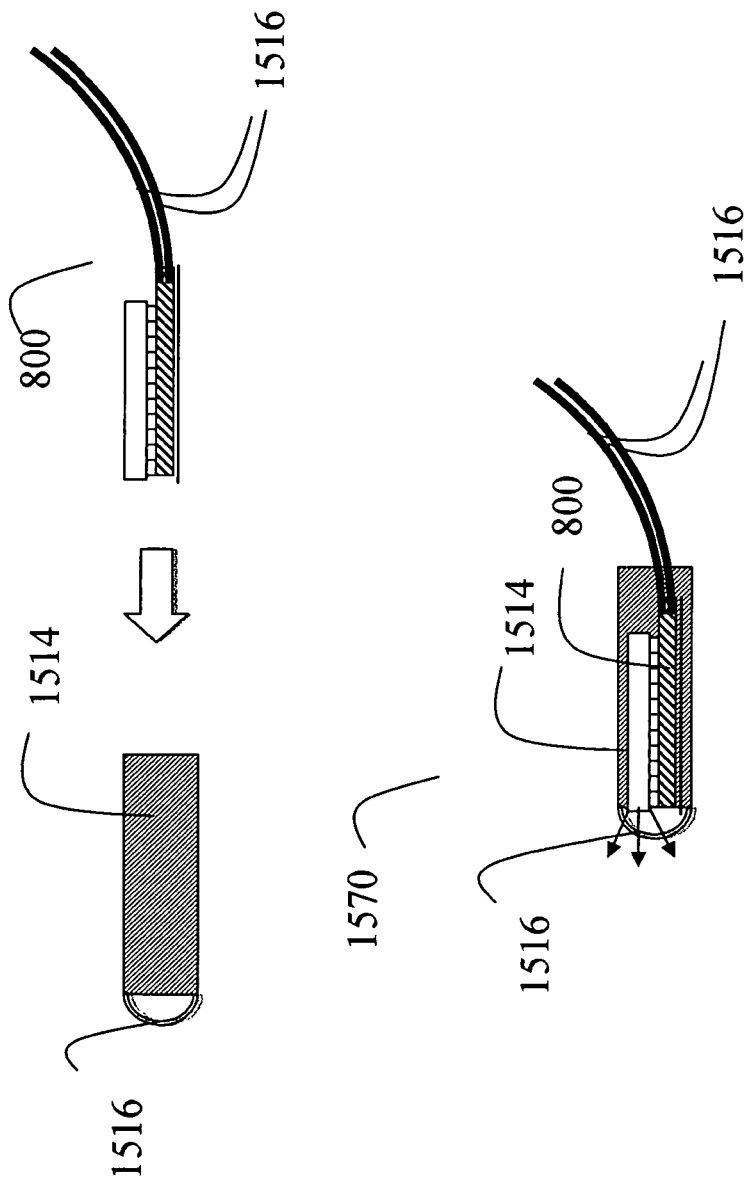
FIG. 15e illustrates the OE LED array illumination module from FIG. 8 being inserted into a rectangular protective cover with a hemispherical optically transparent window.

FIG. 15e illustrates OE illumination module 800 of FIG. 8, being inserted in a single use protective cover 1514, with sealed hemispherical window 1516. OE illumination modules 800, equipped with micro-fluidic heat slug, can be plugged into the distal end of a flexible endoscope with means to provide the OE illumination module 800 with cooling fluidic lines 1516.

Figure 15F:
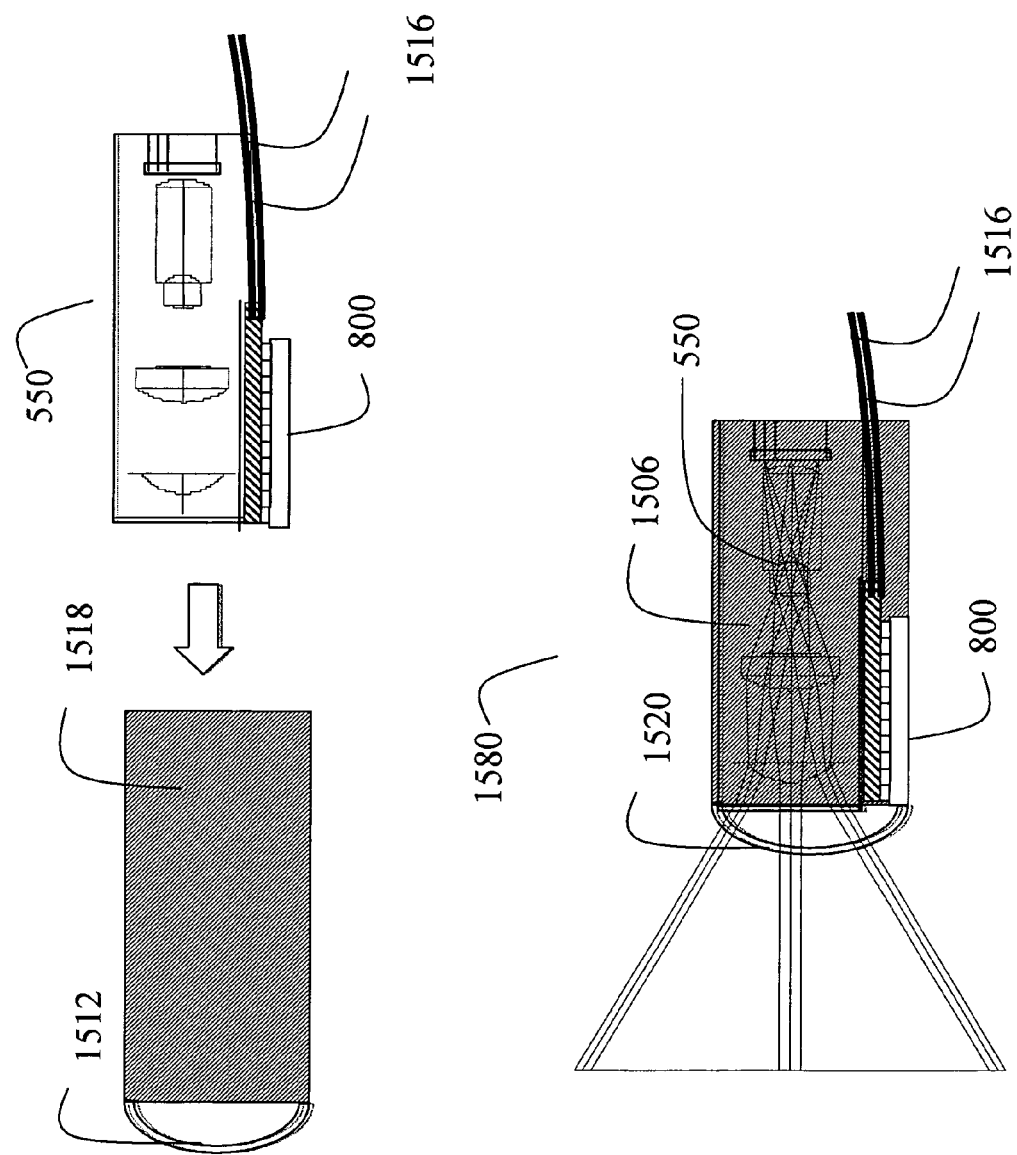
FIG. 15f illustrates the pluggable cylindrical shape OE vision module depicted in FIG. 5b, and the OE LED array illumination module depicted in FIG. 8 being inserted into cylindrical protective cover with a hemispherical optically transparent window.

FIG. 15f illustrates OE vision module 550 of FIG. 5b along with LED array illumination module 800 of FIG. 8 together inserted into sealed protective cover 1518, with sealed hemispherical window 1520.

Figure 16C:
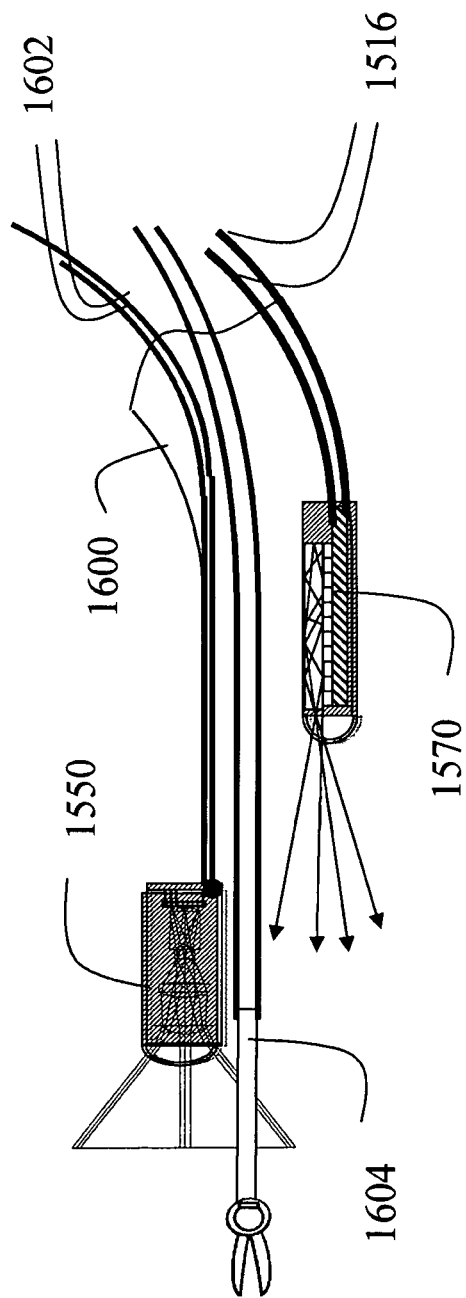
FIGS. 16a and 16b illustrate a medical device equipped with the OE LED array illumination module with its protective cover depicted in FIG. 15e, and the pluggable OE vision module with protective cover in FIG. 15c, being deployed out of the medical device space allowing surgical tool insertion space through the body of the medical device illustrated in FIG. 16c.

FIGS. 16a and 16b illustrate an embodiment, incorporating OE illumination module 1570 at the distal end of a flexible endoscope, and a dynamic deployment of the OE vision module 1550, which is plugged into the deployment mechanism provided at the distal tip of flexible endoscope 1600. In FIG. 16a the OE vision module 1550 is in its "off" or insertion position. In order to deploy the OE vision module 1550, the OE vision module 1550 is flipped over the endoscope tip using actuation cables 1602 actuating the deployment mechanism. Once the OE vision module 1550 is deployed ("on" position) the 1550 OE vision module is flipped into position around the endoscope distal tip as shown in FIG. 16b. The deployment of the OE vision module at the distal tip of the endoscope, opens the area within the endoscope, for insertion and use of various surgical tools through the flexible endoscope body. FIG. 16c, represents such use of the now available space inside the scope body by a surgical tool 1604, where at the end of surgical procedure the surgical tool 1604 is removed and the OE vision module 1550 is flipped back into the position depicted in FIG. 16a, where it is again fully contained within the body of the scope 1600 for withdrawing of the endoscope from the body.

In another embodiment of deployable OE illumination and vision module, FIG. 17a represents an "off" position for the lensed LED illuminator 1204, and OE vision module 1550 as they are stored within the endoscope 1700 free cavity. In an "on" position, LED module 1240 and OE vision module 1550 are deployed in a circular manner, rotating sideways to outside the normal body of the endoscope, opening the area inside the endoscope 1700 cavity for other surgical use such as irrigation, suction or insertion of other visual devices, ultra sound transducers elements, special sensors, mechanical or laser assisted surgical cutters, or tools to perform surgery.

FIGS. 18a and 18b represent anther scheme in storing two OE illumination and vision modules 1580 in their "off" position, within the body and aligned one after the other at the distal end of the endoscope 1800. OE vision modules in FIG. 18a are side ways rotated to deploy out of the body of the endoscope. Then the hollow cylindrical body 1802 is pushed forward towards the distal end of endoscope 1800, aligning the two OE illumination and vision modules 1580 distally at the same position for capturing stereo images of the scene.

Figure 19A:
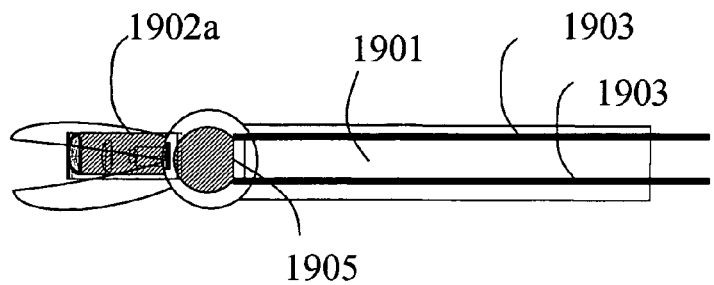
FIGS. 19a, 19b, and 19c illustrate miniature LED illuminators and OE vision modules built into the body of a surgical instrument or tool, with possible hinge type deployment during operation to illuminate and view the surgical site.
Figure 19B:
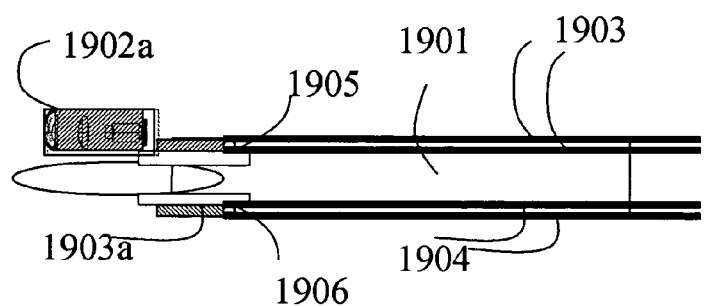
Figure 19C:
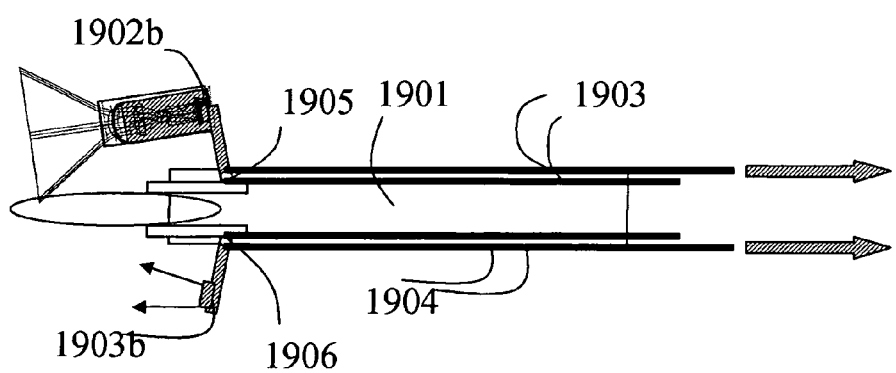

FIGS. 19a through 19c illustrate an exemplary embodiment of miniature LED illumination 1903 or miniature OE vision module 1902 in conjunction with a surgical tool 1901. FIGS. 19a and 19b are side views of the surgical tool 1901, where the LED illumination 1903a and OE vision module 1902a are closely held to the body of the tool in the "off" position. FIG. 19c illustrates the surgical tool as the LED illumination 1903b and vision module 1902b are deployed outwards to their "on" position, away from the tool body using actuation cables 1904 and 1903, and hinge mechanisms 1906 and 1905 respectively.

Incorporating OE vision modules on surgical tools in conjunction with the main endoscope adds much safety to the surgical procedure since it allows the surgeon to have a concurrent multi-direction FOV of the surgical site, in which some of the new visualization on the tools allows for practically orthogonal direction of view with respect to the main endoscope's point of view. In fact, by positioning the OE vision module on tool behind the tool with respect to the main endoscope's point of view, the surgeon is able to view the surgical site that would otherwise be blocked by the position of the tool itself The OE vision systems incorporated on tools also allows for visualization of the tools independent of the main endoscope and without the tools being in the main scope's FOV. They also allow for the constant visual surveillance of the surgical site, even when the main endoscope is pulled out of the body to be switched or wiped clean.

In alternate embodiments of all of the endoscopes, cannulas and other devices described above that use LEDs for illumination, Solid State Laser Diodes (LD) or VSCELs can also be used within the OE illumination and vision module or independently at the distal end of tools, insertion tubes, catheters, imaging scopes, cannulas, etc. Infrared Imaging could use IR solid state light sources to illuminate intra-vein or close tissue diagnostic and surgical procedures. IR detectors and special image sensors with modified optical filters in front of their pixels can be used within EO vision modules for through tissue and blood imaging along with infrared light sources that have appreciable penetration depth in human tissue, blood or other bodily fluids such as urine. Using a high intensity IR source at the surgical or examination site with control over the intensity, radiation pattern, and the direction of illumination helps with the most critical surgical procedures inside the vein, heart and other body organs.

Scanning or other directing mechanical elements could also be used to adjust the direction of illumination and control of the solid state light sources (laser diodes, and LEDs) used in conjunction with a variety of surgical instruments inside the body, where other scanning or non scanning EO vision modules capture elements detect the light. Additionally, since power is provided to the solid state light source at the distal end of the probe or scope, resistive heat from part of the electrical signal can also be used to reduce condensation at the probe or scope window.

By placing the illumination light sources at close proximity to the object inside the body in diagnostic or surgical procedures, the losses in conjunction with the transmission of light from the external source to the surgical site are eliminated. Thus, light sources that have equal efficiency in converting electrical power to useful light, can be operated in much lower input power, eliminating the need for sophisticated power and heat management. Power and control signals transmitting through appropriate wires and flex circuitry, can be easily routed along the tool or endoscope body to the light source and OE vision module.

FIG. 20a shows another embodiment of pluggable OE illumination and vision module 1560 with protective cover and hemispherical window, can be achieved by plugging it into a handheld visualization tool handle 2002. Various illumination sources 504 (LEDs or VCSEL sources) of various spectral characteristics (UV, visible, IR, narrow or wide spectral band) can be used in the vision module 560, to apply different functionality to the handheld device. For example the device can be used for detection of pre cancerous cells by inducing bio-fluoresces using blue light illumination in the mouth cavity, with or without use of contrast agents. The hand held endoscopes of this type can also be equipped with electrical connection 1302, for power and imaging signal transfer, or be battery operated, with optical 1304 or wireless link 1306, such as described in FIG. 13, for transfer data.

FIG. 20b illustrates another embodiment of such hand held visualization tool, with modified tip optics for the OE illumination and vision module 560, where 45 degree prism 2004 at the tip allows side viewing capability in direction 2006, normal to the handheld device axis.

Miniature, optical components such as lenses, mirrors, beam splitters, polarizers, waveplates, etc. can also be used in conjunction with solid state light sources (e.g., laser diodes and LEDs) and solid state image sensors in OE illumination and vision modules to further manipulate the illumination characteristics of the light. Lenses for example, can be used to direct the light to larger or smaller areas of the scene, or focusing the beam to a small area on the object depending on the application. Special lenses and opto-electronic schemes can be used to change the FOV and magnification of the EO vision module.

Polarization characteristics of the solid state laser or polarized LED light output can also be used in special detection schemes, where depth perception or other biological imaging characteristics that depend on the polarization of the light can be better perceived, similar to polarized microscopy.

Where the space within the endoscope body allows for an accommodation of a larger OE module with higher level of device integration, OE vision modules could also contain other functional opto-electronics, electromechanical devices, sensors and actuators.

Figure 21:
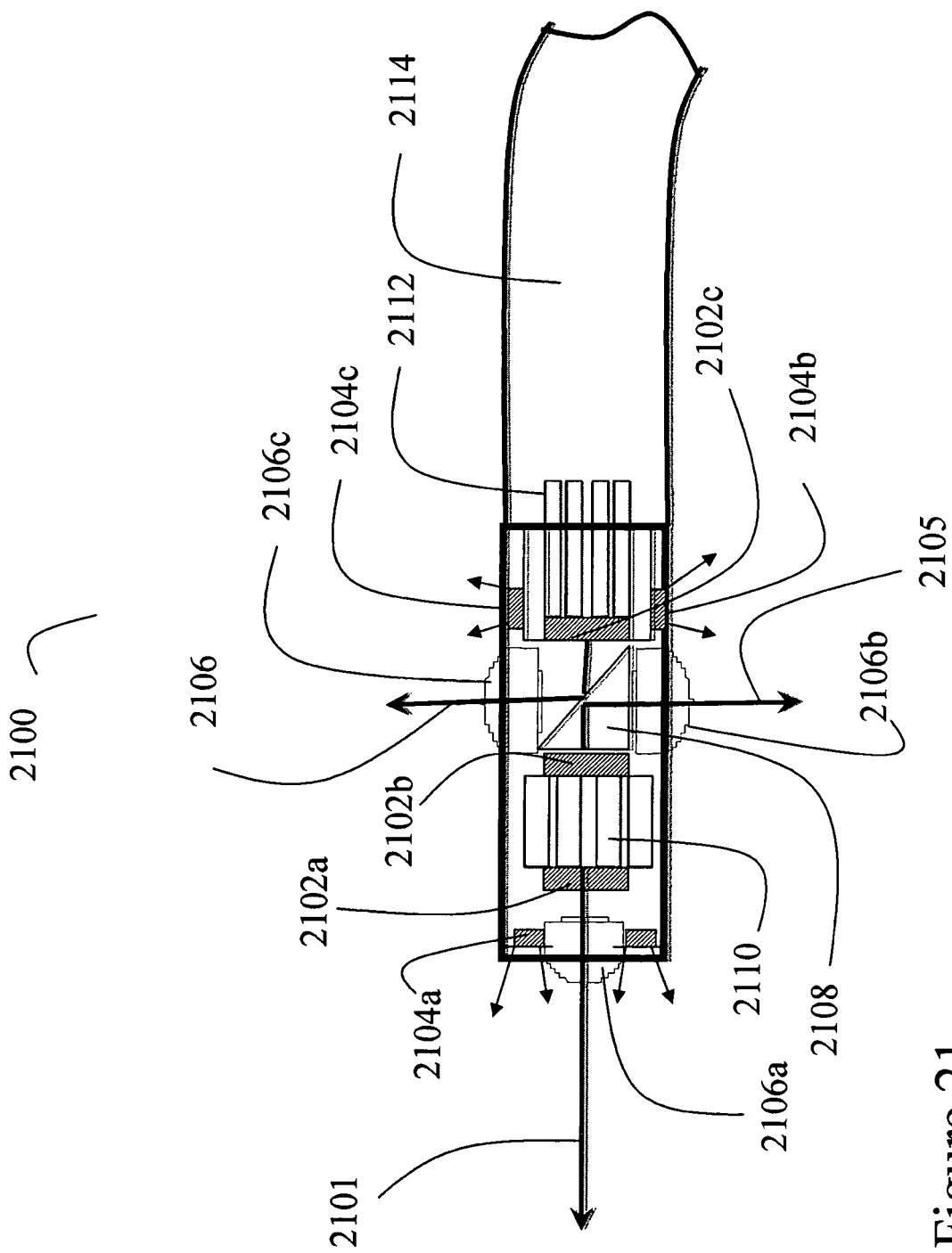
FIG. 21 represents a pluggable multi-sensor and illuminator OE module at the tip of a flexible medical device with front as well as side viewing capability and FIG. 22 illustrates an OE vision module with dual optical vision system and overlapping FOV, where the combined image is electronically stitched over the FOV overlap region to achieve much larger overall FOV.

FIG. 21 represents a pluggable multi vision OE illumination and vision module 2100, that can be plugged into the tip of flexible endoscope 2114. Front viewing is made possible by imaging lens 2106a and image sensor 2102a. The scene in front is viewed in 2101 direction as it's illuminated by dual solid state light sources 2104a, while solid state light sources 2104b and 2104c illuminate the sides of the endoscope. Side vision in directions 2105 and 2106 are concurrently made possible by imaging optics 2106b and 2106c, and imaging sensors 2102b and 2102c. Mirrored beam splitter 2108 is used to direct the side view images on to the appropriate sensors 2102b and 2102c. Appropriate electronics 2110 are housed within the same housing.

Using miniature OE elements and a maneuverable endoscope body such as 2100, multi directional viewing can be made possible in trans-luminal diagnostic procedures. The side viewing OE elements can be extended with the space available for quad viewing in all sides. Other OE illumination and visual modules can also be incorporated at different positions in length of the 2114 endoscope. Using UV and deep blue illumination sources could be used in this geometry for detecting pre-cancer lesions due to various bio-fluorescence tissue activities in natural orifices. Using IR VCSELs as illumination sources would enable inter artery endoscopy.

Figure 22:
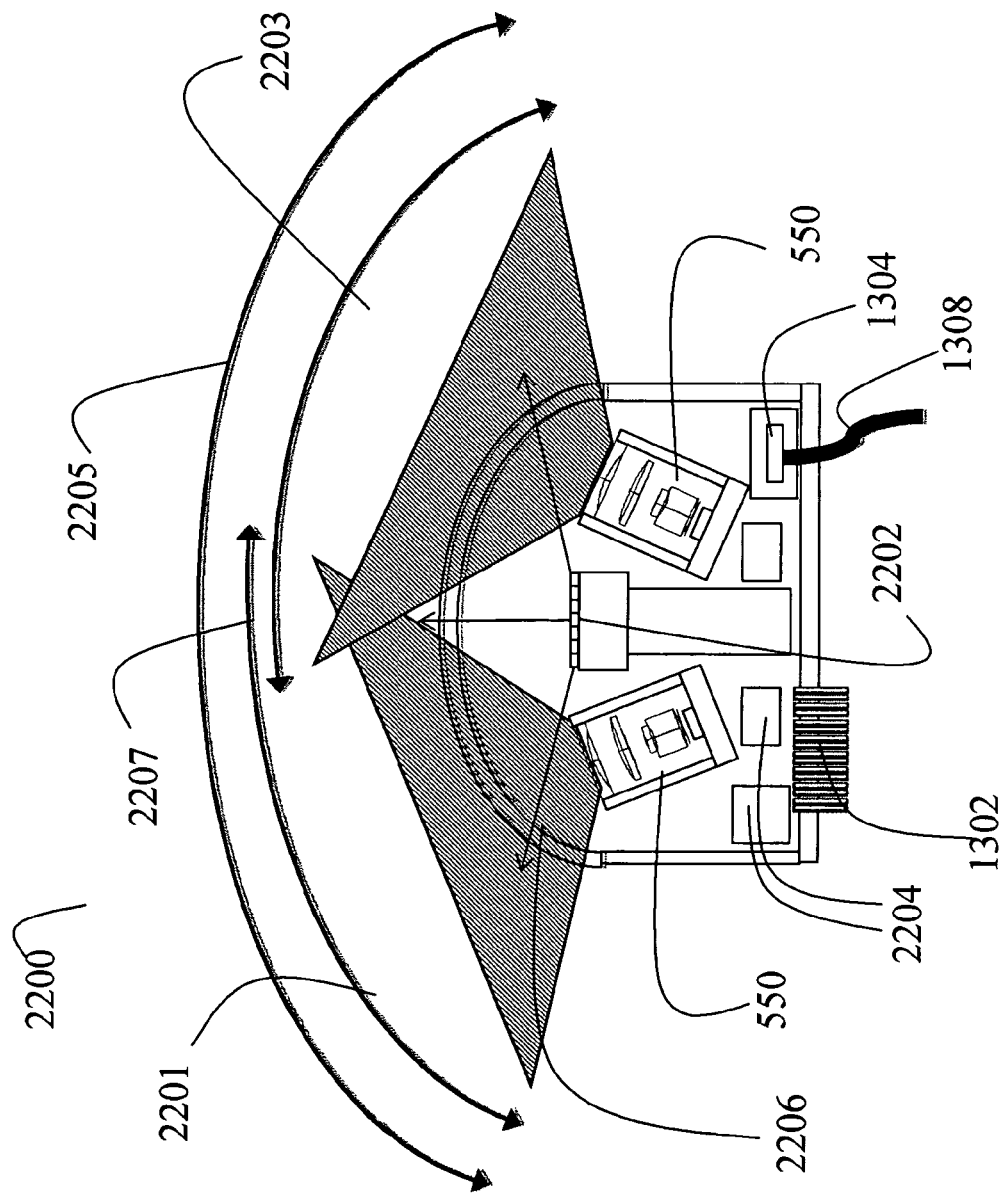

FIG. 22 represents an alternate embodiment of an OE vision module where multiple vision systems 550 within an OE vision module are used to obtain a combined hyper field of view. As wide angle array LED illuminator 2202 illuminates the area through the curved window 2206, the overlapping (2207) imaging FOV 2201 and 2203 of OE vision systems 550 are combined by electronic image stitching to obtain a much larger field of view 2205. Electronic components 2204 can be used within the module for image processing or the dual image sensor data can be sent to the control unit by the electrical connection 1302 or optical link 1304 and fiber optic line 1308. Although not depicted in FIG. 22, reflective mirrors or optical prisms can also be used in at the imaging optics path to direct the direction of view to adjacent areas on the object producing an appropriately overlapped field of view for successful image stitching.

In embodiments of the invention described herein, one or more additional opto-electronic detectors can be implemented in the OE vision module to allow direct detection of secondary information about the imaging field. For instance, RGB and/or IR detectors can be used to detect the overall illumination and imaging spectral quality. With changing scene, the information collected from the main imaging sensor or the additional detectors can be used to tune the illumination light spectrally, control the flux for the most optimum image detection, control the image capture electronics and data collection, and the like or any combination thereof in a complete feedback loop.

Alternately or additionally, user-specific information can be used to setup the overall illumination and image capture tuning. For example, the contrast of the image can be tuned to enhance the visibility for certain users with color contrast detection deficiencies.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A device for insertion into a body cavity, the device comprising:
   a hollow tubular portion having a proximal end and a distal end, the distal end including a flexible region configured to be at least partially inserted into the body cavity and made void to provide access space inside the body;
   an illumination module configured to be removably plugged in to the distal end of the hollow tubular portion such that the illumination module is disposed in the flexible region of the distal end of the hollow tubular portion;
   digital vision module having a cylindrical shape with a base and a lateral surface, the digital vision module separate from the illumination module and configured to be removably plugged in to the distal end of the hollow tubular portion;
   a hinge positioned adjacent to the base and the lateral surface of the digital vision module distal to enable the digital vision module to rotate longitudinally along a single plane that includes the hollow tubular portion between an insertion position and a deployed position, wherein the digital vision module disposed at the distal end of the hollow tubular portion completely outside the hollow tubular portion in the deployed position to open a void extending along an entire length of the hollow tubular portion; and
   a power source electrically coupled to the opto-electronic digital vision and illumination modules.

2. The device of claim 1, wherein the device is any one of an endoscope tool, a cannula, a surgical tool, or a borescopy tool.

3. The device of claim 1, wherein the digital vision and illumination modules are configured to be removably plugged in to a deployment mechanism positioned at the hollow tubular portion.

4. The device of claim 3, wherein the removable digital vision and illumination modules are positioned in a fully sealed and dry air filled housing within the hollow tubular portion behind an airtight optical window.

5. The device of claim 4, wherein the fully sealed and dry air filled housing includes one or more moisture absorbing elements to maintain the air dry.

6. The device of claim 3, wherein the digital vision module and the illumination module are independently and removably covered with a fully sealed protective cover and a sealed optical window in front of optical illumination and imaging paths of the digital vision module and the illumination module.

7. The device of claim 3, wherein the at least one of the digital vision and illumination modules is exchangeable with one or more additional exchangeable vision and illumination modules, each module including a different solid state electro-optic element or a combination of different solid state electro-optic elements.

8. The device of claim 1, wherein the illumination module emits a wavelength that is at least one of red, green, blue, ultraviolet (UV), infrared (IR), or white, or a combination thereof.

9. The device of claim 8, wherein the illumination module is configured to emit ultraviolet or deep blue light to induce bio-fluorescence of one or more areas of the body cavity.

10. The device of claim 8, wherein digital spectral images collected by the digital vision module are processed further to perform structural analysis on type of tissue.

11. The device of claim 1, wherein the linear array of light-emitting devices is coupled into a rectangular light guide.

12. The device of claim 1, wherein at least one of the illumination and digital vision modules is coupled peripherally to the hollow tubular portion by electrical lines, and an actuation mechanism, and wherein removably plugging the illumination and digital vision modules in to the hollow tubular portion establishes an electrical connection to the illumination and digital vision modules.

13. The device of claim 1, wherein the entire inside diameter of the hollow tubular portion is kept open and hollow, to allow access to a distal tip inside the body cavity, and enable other functionalities such as insertion of independent surgical tools, providing suction or irrigation inside the device.

14. The device of claim 1, wherein the illumination module includes an array of LED illuminators with similar or various wavelengths coupled into a common long light guide to transmit the combination light to the distal end of the hollow tubular portion of the device.

15. The device of claim 1, further comprising at least one electrical line disposed within the void and extending along the entire length of the hollow tubular portion and electrically coupling the power source to each of an LED illuminator and a camera of the digital vision and illumination modules.

16. The device of claim 15, wherein the at least one electrical line disposed within the void enables manipulation of the digital vision and illumination modules by movement within the void.

17. The device of claim 1, wherein the digital vision module is spaced apart from the illumination module at the distal end and is rotatably attached to a tip of the distal end such that the digital vision module may be rotated about the tip.

18. The device of claim 1, wherein the linear array of light-emitting devices includes a plurality of the light-emitting devices spaced apart from one another in a longitudinal direction along the length of the hollow tubular portion.

19. A device for insertion into a body cavity, the device comprising:
a flexible tubular portion having a proximal end and a distal end, the distal end configured to be at least partially inserted into the body cavity and including a void extending along an entire length of the flexible tubular portion to provide access to inside the body;
an illumination module configured to be removably plugged in to the distal end of the hollow tubular portion such that the illumination module is disposed over a first surface in the flexible tubular portion proximate the distal end and including a plurality of light sources disposed in a linear array;
a digital image capture device separate from the illumination module and having a cylindrical shape with a base and a lateral surface disposed within a protective cover, the digital image capture device configured to be removably plugged in to the distal end of the hollow tubular portion;
a hinge positioned adjacent to the base and the lateral surface of the digital vision module distal to enable the digital vision module to rotate longitudinally along a single plane that includes the hollow tubular portion between an insertion position and a deployed position, the digital image capture device disposed over a second surface in the flexible tubular portion opposing the first surface in the insertion position and disposed completely outside the distal end of the flexible tubular portion in the deployed position such that the digital image capture device is separate and spaced apart from the illumination module and at least a portion of the void remains unobstructed along the entire length of the flexible tubular portion; and
a power source electrically coupled to the digital image capture device.

20. The device of claim 19, further comprising at least one of a detecting element and a manipulating element disposed in the flexible tubular portion.

21. The device of claim 20, wherein the illumination module, the detecting element, the digital image capture device, and the manipulating element are removable from the flexible tubular portion.

22. The device of claim 20, wherein the illumination module includes multiple illumination and imaging electro-optic elements and their associated optics, the multiple illumination and imaging electro-optic elements and their associated optics being configured to view multiple directions of view with respect to a longitudinal axis of the flexible tubular portion to collect multiple images, and wherein the multiple images are electronically stitched together to achieve a substantially larger field of view.

23. The device of claim 19, wherein the illumination module includes a plurality of solid state electro-optic elements of various wavelengths as the light source, wherein the plurality of electro-optic elements are electrically linked to the digital image capture device, and wherein the plurality of electro-optic elements are time synchronized with the digital image capture device to provide a color image or appropriately captured multispectral digital images for further processing.

24. The device of claim 23, wherein at least two of the plurality of solid state electro-optic elements are configured to emit infrared light of different spectral ranges, including at least a first infrared spectral range and a second infrared spectral range, enabling the display of depth-specific two-dimensional digital image information obtained by individually collecting light within the first infrared spectral range and light within the second infrared spectral range.

25. The device of claim 24, wherein the depth-specific two-dimensional digital image information can be used to construct a three-dimensional digital image of the body cavity or of an object within the body cavity.

26. The device of claim 19, wherein the digital vision module and the illumination module are electrically coupled to the flexible tubular portion to supply electrical power to the digital vision module and the illumination module and transmit digital imaging signals out of the digital vision module.

27. The device of claim 26, wherein the plurality of light sources disposed in the linear array comprises a linear array of light-emitting devices on a substrate disposed over and in contact with a heat slug including a plurality of micro-fluidic cooling channels.

28. The device of claim 27, wherein one or more multiplexed optical transmitters and receiver units in single or multiple wavelengths, are connected between the digital image capture device and an external control unit using a multimode optical fiber in a single or bidirectional optical communication link.

29. The device of claim 19, further comprising an imaging window disposed in the distal end of the flexible tubular portion, wherein conductive heat generated from the plurality of light sources directed to the imaging window to prevent condensation on the imaging window.

30. The device of claim 19, wherein the illumination module is at least partially conductively coupled to the flexible tubular portion to conduct heat away from the illumination module and the digital image capture device.

31. The device of claim 30, wherein the flexible tubular portion further includes at least one of heat pipes and microchannels for conveying a cooling fluid to transfer heat from the illumination module to the proximal end of the flexible tubular portion outside the body cavity.

32. The device of claim 19, wherein the digital image capture device and the illumination module are configured to be inserted into the body independent of one another.

* * * * *